United States Patent [19]

Scheuble et al.

[11] Patent Number: 5,055,221

[45] Date of Patent: * Oct. 8, 1991

[54] SMECTIC LIQUID-CRYSTALLINE PHASES

[75] Inventors: Bernhard Scheuble, Yokohama; Klaus Bofinger, Mühltal; Reinhard Hopf, Heringen; Axel Pausch, Seeheim; Rudolf Eidenschink, Münster; Joachim Krause, Dieburg; Andreas Wächtler, Griesheim, all of Fed. Rep. of Germany

[73] Assignee: Merck Patent Gesellschaft Mit Beschrankter Haftung, Darmstadt, Fed. Rep. of Germany

[ * ] Notice: The portion of the term of this patent subsequent to Apr. 3, 2007 has been disclaimed.

[21] Appl. No.: 361,068

[22] Filed: Jun. 5, 1989

Related U.S. Application Data

[63] Continuation of Ser. No. 10,094, filed as PCT EP86/00294 on May 16, 1986, published as WO86/07085 on Dec. 4, 1986, abandoned.

[30] Foreign Application Priority Data

May 24, 1985 [DE] Fed. Rep. of Germany ....... 3518734

[51] Int. Cl.$^5$ .............................................. C09K 19/34
[52] U.S. Cl. ........................... 252/299.61; 252/299.63; 252/299.01; 252/299.6; 359/104
[58] Field of Search ............. 252/299.5, 299.61, 299.6, 252/299.01, 299.63; 350/350 S

[56] References Cited

U.S. PATENT DOCUMENTS

| | | | |
|---|---|---|---|
| 4,311,610 | 1/1982 | Zaschke et al. | 252/299.61 |
| 4,358,393 | 11/1982 | Zaschke et al. | 252/299.61 |
| 4,460,770 | 7/1984 | Petrzilka et al. | 252/299.61 |
| 4,510,069 | 4/1985 | Erdenschink et al. | 252/299.61 |
| 4,512,636 | 4/1985 | Andrews et al. | 252/299.61 |
| 4,593,857 | 6/1986 | Sugimori et al. | 252/299.63 |
| 4,601,846 | 7/1986 | Demus et al. | 252/299.61 |
| 4,621,901 | 11/1986 | Petrzilka et al. | 252/299.61 |
| 4,622,165 | 11/1986 | Kane et al. | 252/299.01 |
| 4,623,477 | 11/1986 | Ogawa et al. | 252/299.61 |
| 4,640,795 | 2/1987 | Ogawa et al. | 252/299.61 |
| 4,642,199 | 2/1987 | Sugimori et al. | 252/299.61 |
| 4,659,500 | 4/1987 | Sugimori et al. | 252/299.61 |
| 4,659,502 | 4/1987 | Fearon et al. | 252/299.61 |
| 4,668,426 | 5/1987 | Demus et al. | 252/299.61 |
| 4,676,604 | 6/1987 | Petrzilka et al. | 252/299.61 |
| 4,683,078 | 7/1987 | Sugimori et al. | 252/299.61 |
| 4,684,220 | 8/1987 | Shionozaki et al. | 252/299.61 |
| 4,704,227 | 11/1987 | Krause et al. | 252/299.61 |
| 4,713,197 | 12/1987 | Eidenschink et al. | 252/299.61 |
| 4,721,367 | 1/1988 | Yoshinaga et al. | 252/299.61 |
| 4,752,414 | 6/1988 | Eidenschink et al. | 252/299.61 |
| 4,753,752 | 6/1988 | Raynes et al. | 252/299.61 |
| 4,882,082 | 11/1989 | Eidenschink et al. | 252/299.61 |
| 4,891,151 | 1/1990 | Wingen et al. | 252/299.61 |
| 4,911,863 | 3/1990 | Sage et al. | 252/299.61 X |
| 4,913,837 | 4/1990 | Gray et al. | 252/299.61 |

FOREIGN PATENT DOCUMENTS

| | | | |
|---|---|---|---|
| 56501 | 7/1982 | European Pat. Off. | 252/299.61 |
| 84194 | 7/1983 | European Pat. Off. | 252/299.61 |
| 149238 | 7/1985 | European Pat. Off. | 252/299.61 |
| 206228 | 12/1986 | European Pat. Off. | 252/299.61 |
| 225195 | 6/1987 | European Pat. Off. | 252/299.61 |
| 3315295 | 10/1984 | Fed. Rep. of Germany | 252/299.61 |
| 3404116 | 8/1985 | Fed. Rep. of Germany | 252/299.61 |
| 3404117 | 8/1985 | Fed. Rep. of Germany | 252/299.61 |
| 3500909 | 7/1986 | Fed. Rep. of Germany | 252/299.61 |
| 3506446 | 8/1986 | Fed. Rep. of Germany | 252/299.61 |
| 3515373 | 11/1986 | Fed. Rep. of Germany | 252/299.61 |
| 3515633 | 11/1986 | Fed. Rep. of Germany | 252/299.61 |
| 3600052 | 7/1987 | Fed. Rep. of Germany | 252/299.61 |
| 245912 | 1/1981 | German Democratic Rep. | 252/299.61 |
| 56-164170 | 12/1981 | Japan | 252/299.61 |
| 56-164171 | 12/1981 | Japan | 252/299.61 |
| 60-78972 | 5/1985 | Japan | 252/299.61 |
| 61-17571 | 1/1986 | Japan | 252/299.61 |
| 61-167671 | 7/1986 | Japan | 252/299.61 |
| 61-215375 | 9/1986 | Japan | 252/299.61 |
| 61-246168 | 11/1986 | Japan | 252/299.61 |
| 61-260067 | 11/1986 | Japan | 252/299.61 |
| 61-281192 | 12/1986 | Japan | 252/299.61 |
| 62-00071 | 1/1987 | Japan | 252/299.61 |
| 62-22889 | 1/1987 | Japan | 252/299.61 |
| WO86/00087 | 1/1986 | PCT Int'l Appl. | 252/299.61 |
| WO86/00067 | 1/1986 | World Int. Prop. O. | 252/299.61 |
| WO86/06401 | 11/1986 | World Int. Prop. O. | 252/299.61 |

OTHER PUBLICATIONS

Zaschke, H., Advances in Liquid Crystal Research & Appl., Bata, L., Ed., Pergamon Press, Oxford, pp. 1059–1074 (1980).

(List continued on next page.)

Primary Examiner—John S. Maples
Assistant Examiner—Richard Treanor
Attorney, Agent, or Firm—Millen, White & Zelano

[57] ABSTRACT

Compounds of the formula I,

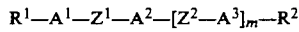

$$R^1-A^1-Z^1-A^2-[Z^2-A^3]_m-R^2 \qquad I$$

in which $R^1$, $R^2$, $A^1$, $A^2$, $A^3$, $Z^1$, $Z^2$ and m have the meaning specified in patent claim 1, are suitable as components of smectic liquid-crystalline phases.

11 Claims, No Drawings

OTHER PUBLICATIONS

Green, D. C. et al., IBM Tech. Discl. Bull., vol. 15, No. 8, pp. 2467–2468 (Jan. 1973).

Pavluchenko, A. I. et al., J. De Physique, Coll. C3, Suppl. No. 4, vol. 40, pp. 63-1-4 (Apr. 1979).

Demus, D. et al., Flüssige Kristalle in Tabellen II, VEB Deutscher Verlag Für Grundstoff Industrie, Leipzig, pp. 344–400 (1984).

Gray, G. W. et al., Liquid Crystals & Plastic Crystals, vol. 1, John Wiley & Sons, N.Y., pp. 165, 166, 142, 143 (1974).

C. Escher, "A Promising Material for Liquid Crystal Displays (LCD): Ferroelectric Smectic Liquid Crystals (FLC)", Kontakte, 2/86, pp. 3–12.

SMECTIC LIQUID-CRYSTALLINE PHASES

This application is a continuation of application Ser. No. 07/010,094, filed as PCT EP86/00294 on May 16, 1986, published as WO86/07085 on Dec. 4, 1986 now abn.

The invention relates to the use of compounds of the formula I $$R^1-A^1-A^2-[Z^2-A^3]_m-R^2 \quad\quad I$$

in which
R$^1$ and R$^2$ are in each case an alkyl group, having 1 to 12 C atoms, in which one or more non-neighbouring CH$_2$ groups may also be replaced by —O—, —CO—, —O—CO—, —O—COO—, —CO—O— —and/or —CH=CH—, or one of the radicals R$_1$ and R$_2$ is also H, F, Cl, Br or CN,
A$^1$ is —Pyr—Pyr—Phe—, —Phe—Pyr—, —Pyr—Cy—or —Cy—Pyr—, is pyrimidin-2,5-diyl, pyridin-2,5-diyl, pyrazin-2,5-diyl or pyridazin-3,6-diyl,
Phe is a 1,4-phenylene which is unsubstituted or substituted by one or two F and/or Cl atoms and/or CH$_3$ and/or CN groups,
Cy is trans-1,4-cyclohexylene,
A$^2$ and A$^3$ are in each case trans-1,4-cyclohexylene, or 1,4-phenylene, which is unsubstituted or substituted by one or two F and/or Cl atoms and/or CH$_3$ and/or CN groups, in which one or more CH groups may also be replaced by N,
Z$^1$ is —CH$_2$CH$_2$—, —CO—O—, —O—CO—, —CH$_2$—O—or —OCH$_2$—,
Z$^2$ is —CO—O—, —O—CO—, —CH$_2$CH$_2$—, —CH$_2$O—, —O—CH$_2$— or a single bond, and
m is 0 or 1,
as components of smectic liquid-crystalline phases.

And also smectic liquid-crystalline phases, particularly chiral tilted smectic phases, containing compounds of the formula I.

Chiral tilted smectic liquid-crystalline phases having ferroelectric properties can be prepared by adding one or more tilted smectic phases havng a suitable chiral doping substance to the basic mixtures (L. A. Beresnev et al., Mol. Cryst. Liq. Cryst. 89, 327 (1982); H. R. Brand et al., J. Physique 44 (lett.), L-771 (1983). Such phases can be used as dielectrics for rapidly switching displays, which are based on the principle of SSFLC technology, described by Clark and Lagerwall (N. A. Clark and S. T. Lagerwall, Appl Phys. Lett. 36, 899 (1980); U.S. Pat. No. 4,367,924) based on the ferroelectric properties of the chirally tilted phase. In this phase, the elongated molecules are arranged in layers, the molecules having a tilt angle to the layer perpendiculars. When proceeding from layer to layer, the tilt direction changes through a small angle relative to an axis which is perpendicular to the layers, so that a helical structure is formed. In displays which are based on the principle of SSFLC technology, the smectic layers are arranged perpendicular to the plates of the cell. The helical arrangement of the tilt directions of the molecules is suppressed by a very small spacing of the plates (about 1-2 μm). The longitudinal axes of the molecules are thereby forced to align themselves in a plane parallel to the plates of the cell, two distinct tilt orientations being produced. Switching to and fro between these two states can be accomplished in the liquid-crystalline phase, which has a spontaneous polarization, by applying a suitable electrical alternating field. This switching process is significantly faster than the conventional twisted cells (TN-LCDs), which are based on nematic liquid crystals.

The low chemical, thermal and light stability of the currently available materials having chirally tilted smectic phases (such as, for example, Sc*) is a great disadvantage for many applications. A further disadvantageous property of displays based on the currently available chirally tilted smectic mixtures is that the spontaneous polarization has values which are too small, so that the switching time behaviour of the displays is unfavourably influenced and/or the pitch and the tilt of the phases do not correspond to the requirements of display technology. In addition, the temperature range of the ferroelectric phases is usually too small and is mainly at temperatures which are too high.

It has now been found that the use of compounds of the formula I as components of chirally tilted smectic mixtures can essentially reduce the disadvantages mentioned. The compounds of the formula I are thus extremely suitable as components of chirally tilted smectic liquid-crystalline phases. In particular, especially chemically stable chirally tilted smectic liquid-crystalline phases having favourable ferroelectric phase regions, particularly having broad Sc* phase regions, excellent supercool-ability to temperatures well below 0° C. without crystallization occurring (even phases according to the invention having a melting point above 0° C. can generally be supercooled to well below 0° C.), favourable degree of pitch, and values for the spontaneous polarization which are high for such phases can be prepared with their aid. P is the spontaneous polarization in nC/cm$^2$.

The compounds of the formula I have a broad field of application. Depending on the selection of substituents, these compounds can be used as base materials from which liquid-crystalline smectic phases are composed to a predominant extent; however, compounds of the formula I can also be added to liquid-crystalline base materials from other classes of compounds, for example in order to vary the dielectric and/or optical anisotropy and/or the viscosity and/or the spontaneous polarization and/or the phase regions and/or the tilt angle and/or the pitch of such a dielectric.

The invention thus relates to the use of the compounds of the formula I as components of chirally tilted smectic liquid-crystalline phases. The invention furthermore relates to smectic liquid-crystalline phases, particularly chirally tilted smectic phases, containing at least one compound of the formula I, and also relates to liquid-crystalline display elements, particularly electro-optical display elements, which contain such phases.

For reasons of simplicity, Cy below is a 1,4-cyclohexylene group and Phe is a 1,4-phenylene group which may optionally also be substituted by one or two F and/or Cl atoms and/or CH$_3$ and/or CN groups (=Phe(F), Phe(Cl), Phe(CH$_3$), Phe(CN)).

The compounds of the formula I cover, in particular, compounds of the subformulae Ia, Ib, Ie and if (having three rings), and also Ic, Id, Ig, Ih, Ii and Ij (having four rings):

| | |
|---|---|
| R$^1$—Pyr—Phe—Z$^1$—Phe—R$^2$ | Ia |
| R$^1$—Pyr—Cy—Z$^1$—Phe—R$^2$ | Ib |
| R$^1$—Pyr—Phe—Z$^1$—Phe—Z$^2$—A$^3$—R$^2$ | Ic |
| R$^1$—Pyr—Cy—Z$^1$—Phe—Z$^2$—A$^3$—R$^2$ | Id |
| R$^1$—Phe—Pyr—Z$^1$—Phe—R$^2$ | Ie |
| R$^1$—Cy—Pyr—Z$^1$—Phe—R$^2$ | If |
| R$^1$—Phe—Pyr—Z$^1$—Phe—Z$^2$—A$^3$—R$^2$ | Ig |
| R$^1$—Cy—Pyr—Z$^1$—Phe—Z$^2$—A$^3$—R$^2$ | Ih |

-continued

R¹—Phe—Pyr—Z¹—A²—Z²—Phe—R²    Ii
R¹—Pyr—Phe—Z¹—A²—Z²—Phe—R²    Ij

Amongst these, those of the subformulae Ia, Ic and Ie are preferred.

The preferred compounds of the subformula Ia cover those of the subformulae Iaa to Iae:

R¹—Pyr—Phe—OCH₂—Phe—R²    Iaa
R¹—Pyr—Phe—CH₂CH₂—Phe—R²    Iab
R¹—Pyr—Phe—CH₂O—Phe—R²    Iac
R¹—Pyr—Phe—OCO—Phe—R²    Iad
R¹—Pyr—Phe—COO—Phe—R²    Iae

Amongst these, those of the subformulae Iaa and Iad are particularly preferred. Iae is furthermore preferred.

The preferred compounds of the subformulae Iba to Ibc:

R¹—Pyr—Cy—OCH₂—Phe—R²    Iba
R¹—Pyr—Cy—CH₂CH₂—Phe—R²    Ibb
R¹—Pyr—Cy—CH₂O—Phe—R²    Ibc

Preferred compounds of the subformula Ic are those of the subformulae Ica to Icg:

R¹—Pyr—Phe—OCH₂—Phe—OCO—Cy—R²    Ica
R¹—Pyr—Phe—OCH₂—Phe—OCO—Phe—R²    Icb
R¹—Pyr—Phe—OCH₂—Phe—Pyr—R²    Icc
R¹—Pyr—Phe—OCO—Phe—Phe—R²    Icd
R¹—Pyr—Phe—OCO—Phe—Pyr—R²    Ice
R¹—Pyr—Phe—COO—Phe—Phe—R²    Icf
R¹—Pyr—Phe—COO—Pyr—Phe—R²    Icg

Amongst these, those of the subformulae Ica, Icd, Ice, Icf and Icg, particularly Ice, are particularly preferred.

The preferred compounds of the subformula Ie cover those of the subformulae Iea to Iee:

R¹—Phe—Pyr—OCH₂—Phe—R²    Iea
R¹—Phe—Pyr—CH₂CH₂—Phe—R²    Ieb
R¹—Phe—Pyr—CH₂O—Phe—R²    Iec
R¹—Phe—Pyr—OCO—Phe—R²    Ied
R¹—Phe—Pyr—COO—Phe—R²    Iee

Amongst these, those of the subformula Iea, Ied and Iee are particularly preferred.

The preferred compounds of the subformula If cover those of the subformulae Ifa to Ife:

R¹—Cy—Pyr—OCH₂—Phe—R²    Ifa
R¹—Cy—Pyr—CH₂CH₂—Phe—R²    Ifb
R¹—Cy—Pyr—CH₂O—Phe—R²    Ifc
R¹—Cy—Pyr—OCO—Phe—R²    Ifd
R¹—Cy—Pyr—COO—Phe—R²    Ife

The preferred compounds of the subformula Ig cover those of the subformulae Iga to Igk:

R¹—Phe—Pyr—OCH₂—Phe—Cy—R²    Iga
R¹—Phe—Pyr—OCO—Phe—OCO—Phe—R²    Igb
R¹—Phe—Pyr—OCO—Phe—OCO—Cy—R²    Igc
R¹—Phe—Pyr—OCO—Phe—COO—R²    Igd
R¹—Phe—Pyr—OCO—Phe—COO—Cy—R²    Ige
R¹—Phe—Pyr—COO—Phe—COO—Phe—R²    Igf
R¹—Phe—Pyr—COO—Phe—COO—Cy—R²    Igg
R¹—Phe—Pyr—COO—Phe—OCO—Phe—R²    Igh
R¹—Phe—Pyr—COO—Phe—OCO—Cy—R²    Igi
R¹—Phe—Pyr—COO—Phe—Pyr—R²    Igj

-continued

R¹—Phe—Pyr—OCO—Phe—Pyr—R²    Igk

Amongst these, those of the subformula Igk are particularly preferred.

The preferred compounds of the subformula Ii cover those of the subformulae Iia to Iid:

R¹—Phe—Pyr—OCH₂—Phe—Phe—R²    Iia
R¹—Phe—Pyr—OCH₂—Phe—CH₂O—Phe—R²    Iib
R¹—Phe—Pyr—CH₂O—Phe—Phe—R²    Iic
R¹—Phe—Pyr—OCO—Phe—Phe—R²    Iid

The preferred compounds of the subformula Ij cover those of the subformulae Ija to Ijd:

R¹—Pyr—Phe—OCH₂—Phe—Phe—R²    Ija
R¹—Pyr—Phe—OCO—Phe—Phe—R²    Ijb
R¹—Pyr—Phe—COO—Pyr—Phe—R²    Ijc
R¹—Pyr—Phe—COO—Phe—Phe—R²    Ijd

In the compounds of the formulae above and below, R¹ and R² are preferably alkyl or alkoxy, furthermore oxaalkyl, alkanoyloxy or alkoxycarbonyl.

A¹ is preferably —Pyr—Phe— or Phe—Pyr—, particularly preferably a structural element selected from the group comprising the formulae 1 to 4:

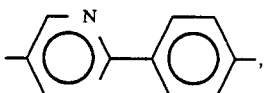

1

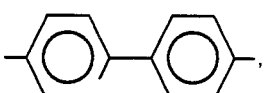

2

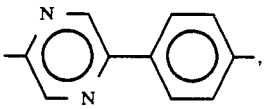

3

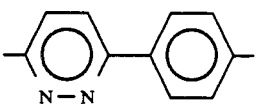

4

The groups of the formulae 1 and 2 are particularly preferred.

A² is preferably unsubstituted 1,4-phenylene or trans-1,4-cyclohexylene.

Z¹ is preferably —OCH₂—, —O—CO— or —CO—O—.

m is preferably 0.

Z² is preferably a single bond, —CO—O— or —O—CO—, particularly preferably —O—CO—.

A³ is preferably Cy or Phe.

The alkyl radicals in the groups R¹ and/or R² may be straight-chain or branched. They are preferably straightchain, have 5, 6, 7, 8, 9, 10, 11 or 12 C atoms and, accordingly, are preferably pentyl, hexyl, heptyl, octyl, nonyl, decyl, undecyl or dodecyl, furthermore methyl, ethyl, propyl or butyl.

If R¹ and/or R² are alkyl radicals in which one ("alkoxy" or "oxaalkyl") or two ("alkoxyalkoxy" or "dioxaalkyl") CH₂ groups are replaced by 0 atoms, then they may be straight-chain or branched. They are preferably straight-chain, have 5, 6, 7, 8, 9, 10, 11 or 12 C atoms and, accordingly, are preferably pentoxy, hexoxy, heptoxy, octoxy, nonoxy, decoxy, undecoxy, dodecoxy, 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl, 1,3-, 1,4-, 1,5-, 1,6-, 2,4-, 2,5-, 2,6-, 3,5-, 3,6 or 4,6-dioxaheptyl, 1,4-dioxaoctyl, 1,4,7-trioxaoctyl, 1,4-dioxanonyl or 1,4-dioxadecyl.

Alkenyl groups in the compounds of the formula I are preferably straight-chain trans-alkenyl groups of the formula

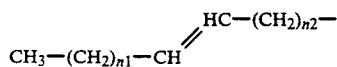

in which n2 is 0 to 10, preferably 2 to 10, and
n1 is 0 to 5, preferably 0.

Compounds of the formula I and of the subformulae above and below having branched wing groups $R^1$ or $R^2$ may occasionally be important because of a higher solubility in the conventional liquid-crystalline base materials, but particularly as chiral doping substances for chirally tilted smectic phases, if they are optically active. However, such compounds are also suitable as components of nematic liquid-crystalline phases, particularly to prevent reverse twist. Branched groups of this type generally contain not more than one chain branch. Preferred branched radicals are isopropyl 2-butyl (=1-methylpropyl), isobutyl (=2-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl and 2-octyloxy.

The asymmetrical carbon atom is preferably linked to two differently substituted C atoms, one H atom and a substituent selected from the group comprising halogen (particularly F, Cl or Br), alkyl or alkoxy having 1 to 5 C atoms in each case, and CN. The optically active organic radical preferably has the formula

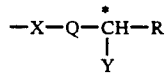

in which

X is —CO—O—, —O—CO—, —O—CO—O—, —CO—, —O—, —S—, —CH═CH—, —CH═CH—COO— or a single bond, Q is alkylene, having 1 to 5 C atoms, in which a $CH_2$ group, not linked to X, may also be replaced by —O—, —CO—, —O—CO—, —CO—O— or —CH═CH—, or a single bond, Y is CN, halogen, methyl or methoxy, and R is an alkyl group, having 1 to 18 C atoms, which is different from Y and in which one or two non-neighbouring $CH_2$ groups may also be replaced by —O—, —CO—, —O—CO—, —CO—O— and/or —CH═CH—.

X is preferably —CO—O—, —O—CO—, —O—, —CH═CH—COO— (trans) or a single bond.

—O—, —CO—O— and —O—CO— are particularly preferred.

Q is preferably alkylene having 1 to 5 C atoms or a single bond, particularly preferably —$CH_2$—, —$CH_2CH_2$— or a single bond.

Y is preferably $CH_3$, —CN or Cl, particularly preferably —CN or Cl.

R is preferably straight-chain alkyl, having 1 to 10 particularly having 1 to 7, C atoms, in which the $CH_2$ group which is linked to the asymmetrical C atom may optionally be replaced by —O—, —O—CO— or —CO—O—.

$R^2$ in formula I is preferably the optically active radical.

Particularly preferred optically active radicals here correspond to the formula

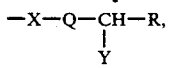

in which X is —O—, -CO-O- or —O—CO-, Q is -CH2- or a single bond, Y is $CH_3$ and R is straight-chain alkyl having 1 to 7 C atoms, in which the $CH_2$ group which is linked to the asymmetrical C atoms is replaced by —O—, —CO—O— or —O—CO—.

Amongst the compounds of the formula I and the subformulae above and below, those are preferred in which at least one of the radicals contained therein has one of the preferred meanings specified. Particularly preferred smaller groups of compounds are those of the formulae I1 to I56:

| | |
|---|---|
| R—Pyr—Phe—OCH₂—Phe—R' | I1 |
| R—Pyr—Phe—CH₂O—Phe—R' | I2 |
| R—Pyr—Phe—OCO—Phe—R' | I3 |
| R—Pyr—Phe—COO—Phe—R' | I4 |
| R—Pyr—Phe—CH₂CH₂—Phe—R' | I5 |
| R—Phe—Pyr—OCH₂—Phe—R' | I6 |
| R—Phe—Pyr—CH₂O—Phe—R' | I7 |
| R—Phe—Pyr—OCO—Phe—R' | I8 |
| R—Phe—Pyr—COO—Phe—R' | I9 |
| R—Phe—Pyr—CH₂CH₂—Phe—R' | I10 |
| R—Pyr—Phe—OCH₂—Cy—R' | I11 |
| R—Pyr—Phe—CH₂O—Cy—R' | I12 |
| R—Pyr—Phe—OCO—Cy—R' | I13 |
| R—Pyr—Phe—COO—Cy—R' | I14 |
| R—Pyr—Phe—CH₂CH₂—Cy—R' | I15 |
| R—Phe—Pyr—OCH₂—Cy—R' | I16 |
| R—Phe—Pyr—CH₂O—Cy—R' | I17 |
| R—Phe—Pyr—OCO—Cy—R' | I18 |
| R—Phe—Pyr—COO—Cy—R' | I19 |
| R—Phe—Pyr—CH₂CH₂—Cy—R' | I20 |
| R—Pyr—Phe—OCH₂—Phe—OCO—Cy—R' | I21 |
| R—Pyr—Phe—OCH₂—Phe—OCO—Phe—R' | I22 |
| R—Phe—Pyr—OCH₂—Phe—OCO—Cy—R' | I23 |
| R—Phe—Pyr—OCH₂—Phe—OCO—Phe—R' | I24 |
| R—Pyr—Phe—OCO—Phe—OCO—Cy—R' | I25 |
| R—Pyr—Phe—COO—Phe—OCO—Cy—R' | I26 |
| R—Phe—Pyr—OCO—Phe—OCO—Cy—R' | I27 |
| R—Phe—Pyr—COO—Phe—OCO—Cy—R' | I28 |
| R—Pyr—Phe—OCO—Phe—OCO—Phe—R' | I29 |
| R—Pyr—Phe—COO—Phe—OCO—Phe—R' | I30 |
| R—Pyr—Phe—OCO—Phe—OCO—Phe—R' | I31 |
| R—Phe—Pyr—COO—Phe—OCO—Phe—R' | I32 |
| R—Pyr—Phe—OCH₂—Phe—Cy—R' | I33 |
| R—Pyr—Phe—OCH₂—Phe—Phe—R' | I34 |
| R—Pry—Phe—OCH₂—Phe—Pyr—R' | I35 |
| R—Pyr—Phe—OCO—Phe—Cy—R' | I36 |
| R—Pyr—Phe—OCO—Phe—Phe—R' | I37 |
| R—Pyr—Phe—OCO—Phe—Pyr—R' | I38 |
| R—Phe—Pyr—OCH₂—Phe—Cy—R' | I39 |
| R—Phe—Pyr—OCH₂—Phe—Phe—R' | I40 |
| R—Phe—Pyr—OCH₂—Phe—Pyr—R' | I41 |

| -continued | |
|---|---|
| R—Phe—Pyr—OCO—Phe—Cy—R' | 142 |
| R—Phe—Pyr—OCO—Phe—Phe—R' | 143 |
| R—Phe—Pyr—OCO—Phe—Pyr—R' | 144 |
| R—Phe—Pyr—OCH$_2$—Pyr—Phe—R' | 145 |
| R—Phe—Pyr—OCO—Pyr—Phe—R' | 146 |
| R—Pyr—Phe—OCO—Phe(F)—R' | 147 |
| R—Pyr—Phe—COO—Phe(F)—R' | 148 |
| R—Phe—Pyr—OCO—Phe(F)—R' | 149 |
| R—Pyr—Phe—CH$_2$O—Phe(F)—R' | 150 |
| R—Pyr—Phe(F)—OCO—Phe—R' | 151 |
| R—Pyr—Phe(F)—OCO—Cy—R' | 152 |
| R—Pyr—Phe(F)—COO—Phe—R' | 153 |
| R—Pyr—Phe(F)—COO—Cy—R' | 154 |
| R—Pyr—Phe—COO—Phe(2-CN)—R' | 155 |
| R—Pyr—Phe—COO—Phe(2-CN, 3-CN)—R' | 156 |

In the formulae I1 to I56 above, R and R' are preferably straight-chain alkyl, alkoxy, alkanoyloxy or alkoxycarbonyl groups having 5 to 12 C atoms in each case.

The abovementioned formulae include the two possible 2,5-positional isomers with respect to the pyridin-2,5-diyl or pyrimidin-2,5-diyl group. This group is preferably linked to $R^1$ in the 5-position.

Compounds of the formula I which have no $S_c$ phases are likewise suitable as components of smectic phases according to the invention.

All compounds of the formula I are prepared by methods which are known per se as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for the reactions mentioned. Use may also be made of variants which are known per se, but which are not described in greater detail here.

By means of routine methods, the expert can take appropriate methods of synthesis from the state of the art (for example Geman Offenlegungsschriften 2,344,732, 2,450,088, 2,429,093, 2,502,904, 2,636,684, 2,701,591 and 2,752,975 concerning compounds having 1,4-cyclohexylene and 1,4-phenylene groups; German Patent 2,641,724 concerning compounds having pyrimidin-2,5-diyl groups; German Offenlegungsschriften 2,944,905 and 3,227,916 concerning compounds having 1,3-dioxan-2,5-diyl groups); DD 160,061 concerning compounds having 1,3-dithian-2,5-diyl groups; U.S. Pat. No. 4,261,652 and 4,219,256 concerning compounds having 1,4-bicyclo(2,2,2)-octylene groups; and German Offenlegungsschrift 3,201,721 concerning compounds having —CH$_2$CH$_2$— bridging members.

The starting materials can also be formed in situ, if desired, in that they are not isolated from the reaction mixture but are instead further reacted immediately to form the compounds of the formula I.

In general, two appropriate sub-compounds (for example (1) and (2) (Equation 1) or (3) and (4) (Equation are condensed to form compounds of the formula I:

Equation 1:

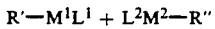

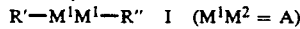

Equation 2:

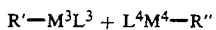

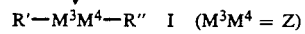

—$M^1L^1$ and —$M^2L^2$ are condensable components which correspond, for example, to malonic acid derivatives (for example malondialdehyde), amidines, aldehydes, 1,3-propanediols and/or 1,3-propanedithiols. $L^1L^2$ are one or more eliminated groups.

—$M^3M^3$ and —$M^4L^4$ are condensable components, for example selected from the group comprising —COOH, —CO— halogen, —OH, —Ometal, —CH$_2$—halogen, —CH$_2$—metal, —CH$_2$—OH, —CH$_2$—O—metal, -metal and -halogen.

$L^3$ and $L^4$ are leaving groups. $L^3L^4$ is an eliminated group such as, for example, H$_2$O, H-halogen or metal-halogen.

However, corresponding intramolecular condensations may also be carried out, in addition, for the synthesis of compounds of the formula I (for example condensation of 1,4-diketones with hydrazine (for example German Offenlegungsschrift 3,238,350) or reaction of a butadiene derivative, for example, with acetylenedicarboxylic acid derivatives (for example Japanese Offenlegungsschrift 58-144,327; Japanese Offenlegungsschrift 58-146,543).

The starting materials are known or can be obtained by methods which are analogous to the preparation of the known compounds.

By routine methods, the expert can take appropriate starting materials and/or methods for the synthesis thereof from the state of the art.

Formula I covers compounds which are mostly known, such as, for example, the preferred pyrimidine derivatives described in German Patent Applications P 3,401,321, P 3,404,116, P 3,500,909 and P 3,506,446, in German Offenlegungsschrift 3,315,295, in European Offenlegungsschrift 84,194 and in U.S. Pat. No. 4,311,610 (European Patent 25,119).

However, the present invention likewise relates to novel pyrimidine derivatives of the formula II

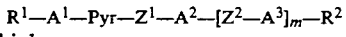

in which
$R^1$ and $R^2$ are in each case an alkyl group, having 1 to 12 C atoms, in which one or two non-neighbouring CH$_2$ groups may also be replaced by —O—, —CO—, —O—CO—, —CO—O— or —CH=CH—, and one of the radicals $R^1$ and $R^2$ is also H, F, Cl, Br or CN, Pyr is pyrimidin-2,5-diyl, $A^2$ and $A^3$ are in each case trans-1,4-cyclohexylene, or 1,4-phenylene which is unsubstituted or substituted by one or two F and/or Cl atoms and/or CH$_3$ and/or CN groups, $A^1$ is 1,4-phenylene which is unsubstituted or substituted by one or two F and/or Cl atoms and/or CH$_3$ and/or CN groups, $Z^1$ is —OCH$_2$— or —O—CO—, $Z^2$ is —CO—O—, —O—CO—, —CH$_2$CH$_2$—, —CH$_2$O—, —O—CH$_2$ or a single bond, and m is 0 or 1, and also to the preparation of the compounds of the formula II, liquid-crystalline phases containing compounds of the formula II and the use thereof as components of liquid-crystalline phases.

The compounds of the formula II have high chemical stability. They are colourless, and easily miscible with all conventional liquid crystals. Their use in liquid-crystalline phases leads to broader mesophase ranges and improved values for the spontaneous polarization in chirally tilted smectic phases. The phases according to the invention are thus very well suited for liquid-crystalline phases for displays which are based on the principle of SSFLC technology. However, they are also further suited for other electro-optical display devices, such as, for example, TN cells or guest/host cells. Here, they serve, in particular, for prevention of reverse twist and for improvement of the elastic constants, besides expanding the mesophase range.

$R^1$ and $R^2$ are preferably alkyl or alkoxy groups having 3 to 10 C atoms in each case. They are preferably straight-chain. However, further preferred compounds are those of the formula II in which one of the groups $R^1$ and $R^2$ is a branched alkyl or alkoxy group.

$A^2$ and $A^3$ are preferably trans-1,4-cyclohexylene or unsubstituted 1,4-phenylene. $A^1$ is preferably unsubstituted 1,4-phenylene. m is preferably 0.

Formula II covers particularly preferred compounds of the subformulae IIa to IIf:

| | |
|---|---|
| $R^1$—Phe—Pyr—OCH$_2$—Phe—$R^2$ | IIa |
| $R^1$—Phe—Pyr—OCO—Phe—$R^2$ | IIb |
| $R^1$—Phe—Pyr—OCH$_2$Cy—$R^2$ | IIc |
| $R^1$—Phe—Pyr—OCO—Cy—$R^2$ | IId |
| $R^1$—Phe—Pyr—OCO—Phe—OCO—Phe—$R^2$ | IIe |
| $R^1$—Phe—Pyr—OCO—Phe—COO—Phe—$R^2$ | IIf |

Amongst these, those of the subformulae IIa, IIb, IIc and IId are particularly preferred. Very particularly preferred compounds are those of the subformulae IIa and IIb.

The compounds of the formula II can be prepared, for example, by esterification of an appropriate carboxylic acid or of one of the reactive derivatives thereof with an appropriate alcohol or a reactive derivative thereof, by etherification of an appropriate hydroxy compound or by reaction of an appropriate amidine or a derivative thereof with a 2-acetylalkanal dialkyl acetal or a reactive derivative thereof.

The present invention furthermore relates to novel tetranuclear compounds of the formula III

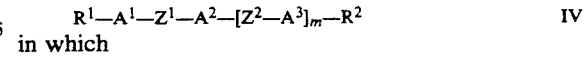

in which $R^1$ and $R^2$ are in each case an alkyl group, having 1 to 12 C atoms, in which one or more non-neighbouring CH$_2$ groups may also be replaced by —O—, —CO—, —O—CO—, —O—COO—, —CO—O— and/or —CH=CH—, $A^1$ and $A^{1'}$ are in each case —Pyr—Phe—, —Phe—Pyr—, —Pyr—Cy— or —Cy—Pyr—, Pyr is a pyrimidin-2,5-diyl, Phe is 1,4-phenylene which is unsubstituted or substituted by one or two F and/or Cl atoms and/or CH$_3$ and/or CN groups, Cy is trans-1,4-cyclohexylene and $Z^3$ is —CO—O— or —CH$_2$O—, and also the preparation of the compounds of the formula III, liquid-crystalline phases containing compounds of the formula III, and the use thereof as components of liquidcrystalline phases.

The compounds of the formula III have high chemical stability. They are colourless, and easily miscible with all conventional liquid-crystals. Their use in liquid-crystalline phases leads to broader mesophase ranges and improved values for the spontaneous polarization in chirally tilted smectic phases. The phases according to the invention are thus very well suited for liquid-crystalline phases for displays which are based on the principle of SSFLC technology. However, they are also further suitable for other electro-optical display devices, such as, for example, TN cells or guest/host cells. Here, they serve, in particular, for prevention of reverse twist and for improvement of the elastic constants, besides expanding the mesophase range.

$R^1$ and $R^2$ are preferably alkyl or alkoxy groups having 3 to 10 C atoms in each case. They are preferably straight-chain. However, further preferred compounds of the formula III are those in which one of the groups $R^1$ and $R^2$ is a branched alkyl or alkoxy group, $A^1$ and $A^{1'}$ are preferably —Pyr—Phe— or —Phe—Pyr—.

Formula III covers particularly preferred compounds of the subformulae IIIa to IIId:

| | |
|---|---|
| $R^1$—Pyr—Phe—COO—Phe—Pyr—$R^2$ | IIIa |
| $R^1$—Pyr—Phe—COO—Pyr—Phe—$R^2$ | IIIb |
| $R^1$—Pyr—Phe—CH$_2$O—Phe—Pyr—$R^2$ | IIIc |
| $R^1$—Pyr—Phe—CH$_2$O—Pyr—Phe—$R^2$. | IIId |

The compounds of the formula III can be prepared, for example, by esterification of an appropriate carboxylic acid or reactive derivatives thereof with an appropriate alcohol or a reactive derivative thereof, by etherification of an appropriate hydroxy compound, or by reaction of an appropriate amidine or a derivative thereof with a 2-acetylalkanal dialkyl acetal or a reactive derivative thereof.

Preferred components of the phases according to the invention are those of the formula IV

in which $R^1$ and $R^2$ are in each case an alkyl group, having 1 to 12 C atoms, in which one or more non-neighbouring CH$^2$ groups may also be replaced by —O—, —CO—, —O—CO—, —O—COO—, —CO—O— and/or —CH=CH—, and one of the radicals $R^1$ and $R^2$ is also H, F, Cl, Br or CN, $A^1$ is 4,4'-biphenylyl, which is unsubstituted or substituted by one or two F and/or Cl and/or Br atoms and/or CH$_3$ and/or CN groups, in which one or more CH groups are replaced by N, $A^2$ and $A^3$ are in each case trans-1,4-cyclohexylene, or 1,4-phenylene, which is unsubstituted or substituted by one or two F and/or Cl atoms and/or Br atoms and or CH$_3$ and/or CN groups, in which one or more CH groups may also be replaced by N, $Z^1$ is —CH$_2$CH$_2$—, —CO—O—, —O—CO—, -CH20-, or -OCH2-, $Z_2$ is —CO—O—, —O—CO—, —CH$_2$CH$_2$—, —CH$_2$O—, —O—CH$_2$— or a single bond, and m is 0 or 1, with the proviso that the compound contains at least one laterally substituted 1,4-phenylene group.

The compounds of the formula IV have high chemical stability. They are colourless, and easily miscible with all conventional liquid crystals. Their use in liquid-crystalline phases leads to broader mesophase ranges and improved values for the spontaneous polarization in chirally tilted smectic phases. The phases according to the invention are thus very well suited for liquid-crystalline phases for displays which are based on the principle of SSFLC technology. However, they are also further suited for other electro-optical display devices, such as, for example, TN cells or guest/host cells. Here, they serve, in particular, for prevention of reverse twist and for improvement of the elastic constants, besides expanding the mesophase range.

$R^1$ and $R^2$ are preferably alkyl or alkoxy groups having 3 to 10 C atoms in each case. They are preferably traight-chain. However, further preferred compounds of the formula III are those in which one of the groups $R^1$ and $R^2$ is a branched alkyl or alkoxy group.

Pyr is preferably linked to Phe in the 2-position.

$Z^1$ is preferably —CO—O—, —O—CO—, —CH$_2$O— or —OCH$_2$—, particularly preferably —O—CO— or —CO—O—.

m is preferably 0.

The laterally substituted phenylene group is preferably a 1,4-phenylene group which is substituted by an F atom (=Phe(F)) or by a CN group (=Phe(CN)).

Further preferred compounds are these having a 2,3-dicyano-1,4-phenylene group (=Phe(CN)2), particularly derivatives of 2,3-dicyanohydroquinone (=Phe(2-CN, 3-CN)).

The formula IV covers particularly preferred compounds of the subformulae IVa to IVm:

| | |
|---|---|
| $R^1$—Pyr—Phe—OCO—Phe(F)—$R^2$ | IVa |
| $R^1$—Pyr—Phe—COO—Phe(F)—$R^2$ | IVb |
| $R^1$—Pyr—Phe—OCO—Phe(CN)—$R^2$ | IVc |
| $R^1$—Pyr—Phe—COO—Phe(CN)—$R^2$ | IVd |
| $R^1$—Phe—Pyr—OCO—Phe(F)—$R^2$ | IVe |
| $R^1$—Phe—Pyr—COO—Phe(F)—$R^2$ | IVf |
| $R^1$—Phe—Pyr—OCO—Phe(CN)—$R^2$ | IVg |
| $R^1$—Phe—Pyr—COO—Phe(CN)—$R^2$ | IVh |
| $R^1$—Pyr—Phe(F)—COO—A$^2$—$R^2$ | IVi |
| $R^1$—Pyr—Phe(F)—OCO—A$^2$—$R^2$ | IVj |
| $R^1$—Pyr—Phe(F)—OCH$_2$—A$^2$—$R^2$ | IVk |
| $R^1$—Phe(F)—Pyr—OCO—A$^2$—$R^2$ | IVl |
| $R^1$—Pyr—Phe—COO—Phe(Z-CN, 3-CN)—$R^2$ | IVm |

In the subformulae IVa, IVc, IVe and IVm, $R^2$ is preferably alkoxy having 4 to 10 C atoms.

Particularly preferred compounds are those of the subformulae IVa, IVb, IVd, IVi, IVj, IVk and IVm, very particularly preferably those of the subformulae IVa and IVb, furthermore IVm.

The compounds of the formula IV can be prepared, for example, by esterification of an appropriate carboxylic acid, or one of the reactive derivatives thereof, using an appropriate alcohol, or one of the reactive derivatives thereof, by eitherification of an appropriate hydroxyl compound by reaction of an appropriate amidine, or a derivative thereof, with a 2-acetyl-alkanal dialkylacetal, or with one of the reactive derivatives thereof, by replacement of the diazonium group in an appropriate diazonium salt by Cl, F or CN, or by reaction of an appropriate chlorine or bromine compound with a cyanide.

All compounds of the formulae II, III and IV, and also those of the corresponding subformulae, are preferred components of the formula I for the smectic phases according to the invention.

The preferred meanings for groups of the formula I also apply analogously to the compounds of the formulae II, III and IV. ding to the invention comprise 2 to 15, preferably 3 to 12, components, including at least one compound of the formula I. The other components are preferably selected from the compounds of the formulae II to IV,

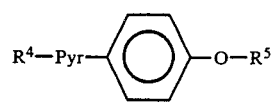

II

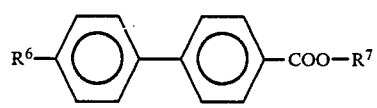

III

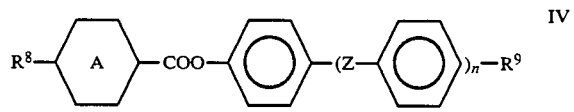

IV in which $R^4$ and $R^5$, in each case independently of one another, are n-alkyl having 5 to 12 C atoms, and $R^6$, $R^7$, $R^8$ and $R^9$, in each case independently of one another, are straight-chain or branched, optionally chiral alkyl, alkoxy, alkoxycarbonyl or alkanoyloxy groups having 5 to 12, particularly having 6 to 10, C atoms. Ring A is 1,4phenylene or trans-1,4-cyclohexylene. n is 0 or 1.

All these substances can be prepared by methods which are known from the literature.

Furthermore preferred are ferroelectric phases, according to the invention, containing at least one compound of the formula V $R^1$—$Q^1$—A—$(Q^2)_q$—$R^2$ in which $R^1$ and $R^2$, in each case independently of one another, are a straight-chain alkyl group, having 1 to 15 C atoms, in which one or more non-neighbouring CH$_2$ groups may also be replaced by —O—, —S—, —CO—, CHCH$_3$—O—, —CHCH$_3$—, CH—halogen—, CHCN—, —O—CO—, —O—COO—, —CO—O— and/or —CH=CH—, A is 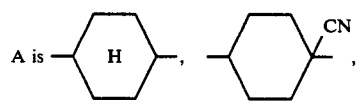

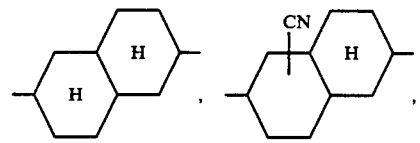

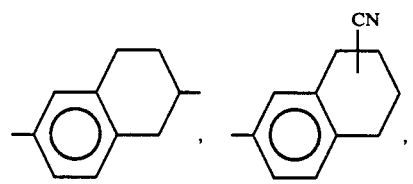

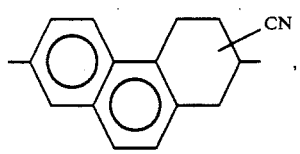

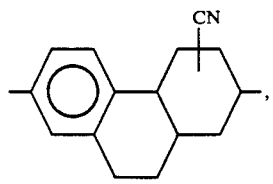

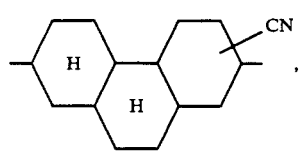

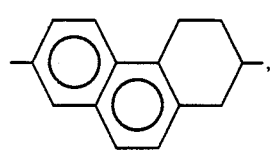

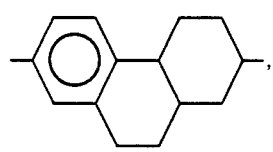

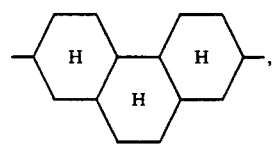

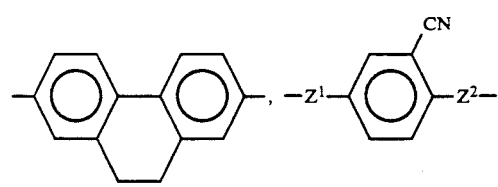

or

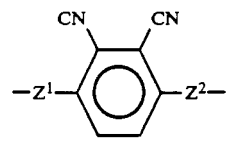

q is 0 or 1,
$Q^1$ and $Q^2$ in each case independently of one another, are —$(A^o—Z^o)_p$—, where
is 1,4-cyclohexylene, which is unsubstituted or mono- or polysubstituted by halogen atoms, $CH_3$ and/or nitrile groups, in which one or two non-neighbouring $CH_2$ groups may also be replaced by —O— and/or —S—, and/or a

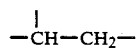

group may be replaced by

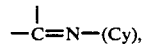

or 1,4-phenylene, which is unsubstituted or mono- or polysubstituted by halogen atoms, $CH_3$ and/ or nitrile groups, in which one or more CH groups may also be replaced by N (Ph), one of the radicals Ao alternatively . . . (sic) 2,6-naphthylene (Na) or tetrahydro-2,6-naphthylene (4H-Na), optionally substituted by halogen or CN, $Z^0$, $Z^1$ in each case independently of one another, and $Z^2$, are —CO—O—, —O—CO—, —$CH_2O$—, —$OCH_2$—, —$CH_2CH_2$—, —$CHCNCH_2$—, —$CH_2$—CHCN— or a single bond, and p is 1, 2 or 3, or, in the case of A=tetra- or octahydrophenanthrene, is alternatively 0, where, in the case of A=

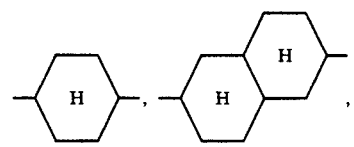

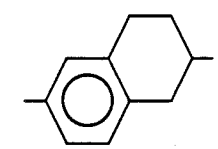

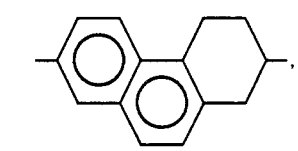

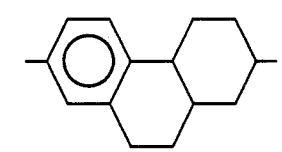

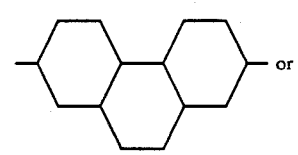

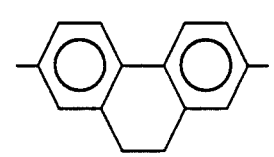

at least one group $Z^0$ is —$CHCNCH_2$— or —$CH_2CH$-CN—, and/or at least one $CH^2$ group in at least one of the groups $R^1$ and $R^2$ is replaced by —CHCN—.

The compounds of the formula V may have straight-chain or branched wing groups $R^1$ and/or $R^2$. Compounds having branched wing groups may be used in the form of the racemate or as optically active compounds. Achiral basic mixtures of compounds of the formula V and, if appropriate, further achiral components may be doped with chiral compounds of the formula I or, additionally, with other chiral compounds in order to obtain chirally tilted smectic phases.

Particularly preferred smaller groups of compounds are those of the formulae V1 to V18:

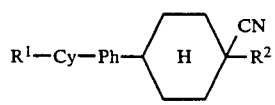
V1

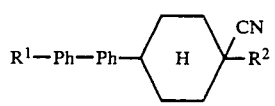
V2

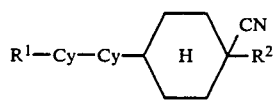
V3

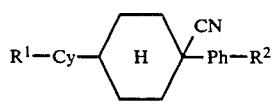
V4

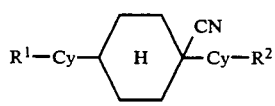
V5

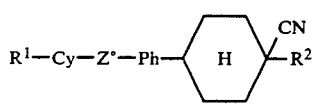
V6

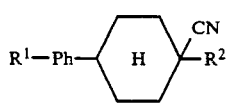
V7

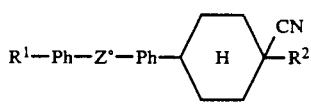
V8

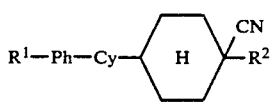
V9

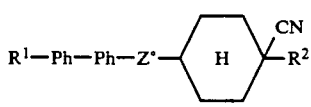
V10

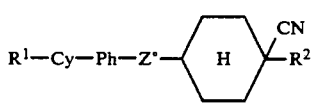
V11

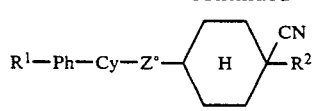
V12

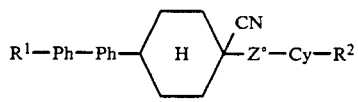
V13

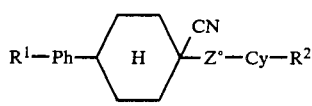
V14

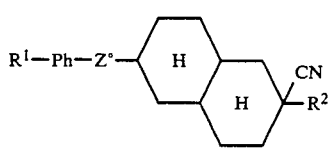
V15

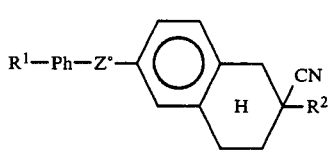
V16

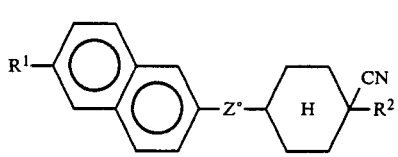
V17

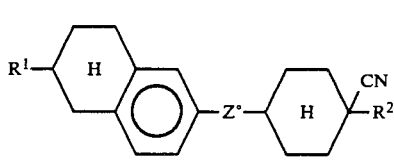
V18

A further particularly preferred smaller group of compounds are (sic) those of the formulae V19 to V22:

   V19

   V20

   V21

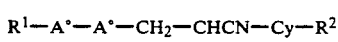   V22 in which r is 0, 1, 2 or 3 and (r+s) is 1 to 14.

Compounds of the formula V which have no $S_c$ phases are likewise suitable as components of smectic phases according to the invention.

All compounds of the formula V are prepared by methods which are known per se as described in the literature (for example in the standard works such as HoubenWeyl, Methoden der Organischen Chemie [Methods of Organic Chemistry], Georg-Thieme-Verlag, Stuttgart), to be precise under reaction conditions which are known and suitable for the reactions mentioned. Use may also be made here of variants which are known per se, but which are not described in greater detail here.

The formula V mainly covers known compounds, such as, for example, the preferred compounds described in German Offenlegungsschriften 3,231,707, 3,319,781, 3,320,024, 3,407,013, 3,443,029, 3,332,690, 3,332,691, 3,332,692, 2,933,563, 2,853,728, 2,613,293, 3,401,320, 3,136,624, 3,040,632, 3,205,766, 2,240,864, 2,937,700, 3,410,734, 3,324,686, European Offenlegungsschrift 0,085,995, European Offenlegungsschrift 0,084,194, DD 116,732, FR 2,425,469, FR 2,419,966, U.S. Pat. Nos. 4,237,026, 3,953,491, 4,225,454 or in H. J. Deutscher et al., J. prakt. Chemie, 321, 569 (1979) and J. C. Dubois et al., Mol. Cryst. Liq. Cryst. 47, 193 (1978).

Suitable components of the phases according to the invention are furthermore compounds of the formula

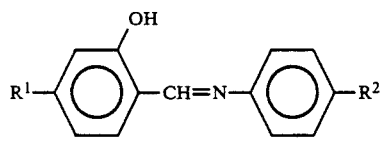

in which $R^1$ and $R^2$ have the meaning specified in the case of formula V.

The phases according to the invention preferably contain at least three, in particular at least five, compounds of the formula I. Particularly preferred chirally tilted smectic liquid-crystalline phases according to the invention are those the achiral basic mixture of which contains, besides compounds of the formula I, at least one other com,ponent having negative or small positive dielectric anisotropy. Further preference is given to phases according to the invention which in the main contain exclusively optically active components. These further component(s) of the achiral basic mixture can make up 1 to 50%, preferably 10 to 25, of the basic mixture. Compounds of the subformulae Va to Vj are suitable as further components having small positive or negative dielectric anisotropy:

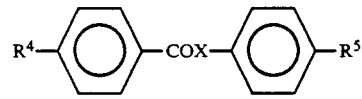 Va

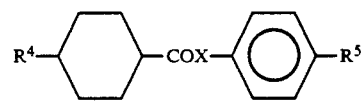 Vb

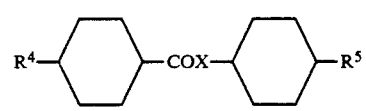 Vc

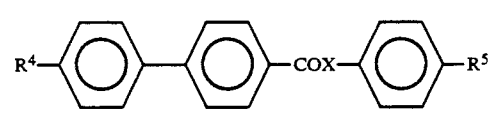 Vd

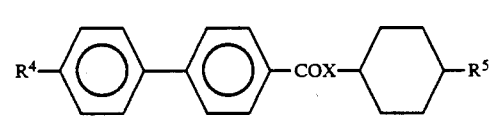 Ve

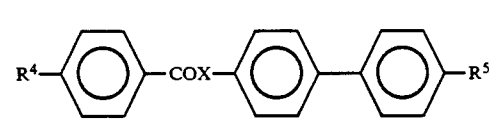 Vf

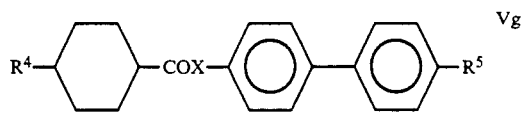 Vg

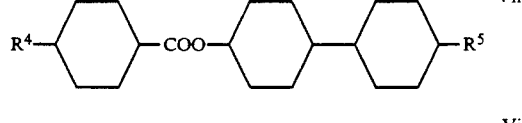 Vh

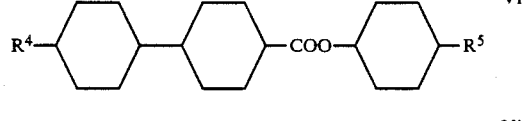 Vi

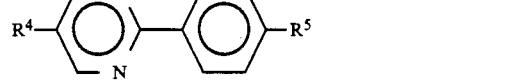 Vj $R^4$ and $R^5$ are in each case preferably straight-chain alkyl, alkoxy, alkanoyloxy or alkoxycarbonyl having 3 to 12 C atoms in each case. X is preferably O.

Particularly perferred compounds are those of the subformulae Va, Vb, Vd and Vf, in which $R^4$ and $R^5$ are in each case straight-chain alkyl or alkoxy having 5 to 10 C atoms in each case.

The compounds of the subformulae Vc, Vh and Vi are suitable as additives for lowering the melting point and are normally added to the basic mixtures in proportions of not more than 5 %, preferably 1 to 3 %. $R^4$ and $R^5$ in the compounds of the subformulae Vc, Vh and Vi are preferably straight-chain alkyl having 2 to 7, preferably 3 to 5, C atoms. A further suitable class of compounds for lowering the melting point in the phases according to the invention is that of the formula

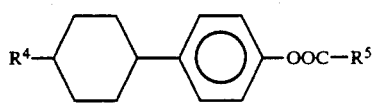

in which $R^4$ and $R^5$ have the preferred meaning specified for Vc, Vh and Vi.

Compounds containing the structural element A, B or C are furthermore suitable as further components having negative dielectric anisotropy.

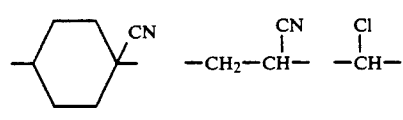

A     B     C

Preferred compounds of this type correspond to the formulae VIa, VIb and VIc:

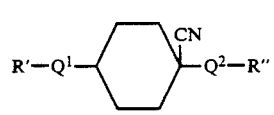 VIa

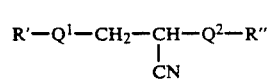 VIb

-continued

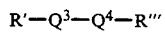 VIc

R' and R" are in each case preferably straightchain alkyl or alkoxy groups having 2 to 10 C atoms in each case. $Q^1$ and $Q^2$ are in each case 1,4-phenylene, trans-1,4-cyclohexylene, 4,4'-biphenylyl, 4-(trans-4-cyclohexyl)-phenyl, trans,trans-4,4'-bicyclohexyl, or one of the groups $Q^1$ and $Q^2$ is also a single bond.

$Q^3$ and $Q^4$ are in each case 1,4-phenylene, 4,4'-biphenylyl or trans-1,4-cyclohexylene. One of the groups $Q^3$ and $Q^4$ may also be 1,4-phenylene, in which at least one CH group is replaced by N. R''' is an optically active radical having an asymmetrical carbon atom of the structure

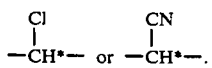

Particularly preferred compounds of the formula VIc are those of the formula VIc':

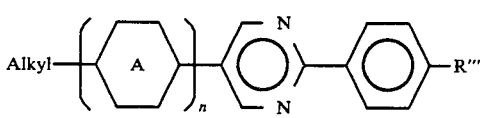 VIc' in which A is 1,4-phenylene or trans-1,4-cyclohexylene, and n is 0 or 1.

The dielectrics according to the invention are prepared in a fashion which is conventional per se. As a rule, the components are dissolved in one another, preferably at elevated temperature.

By means of suitable additives, the liquidcrystalline phases can be modified according to the invention in such a manner that they can be used in all types of liquid-crystal display elements which have hitherto become known.

The following examples are intended to describe the invention without limiting it. m.p.=melting point, c.p.=clear point. Above and below, percentage data are per cent by weight; all temperature data are specified in degrees Celsius. The values for the spontaneous polarization are given for room temperature. Furthermore, C means solid crystalline condition, S means the smectic phase (the index characterizes the phase type), N means the nematic condition, Ch means the cholesteric phase, and I means the isotropic phase. The figure between the two symbols indicates the conversion temperatures in degrees Celsius. "Conventional work-up" means: water is added, the mixture is extracted with methylene chloride, the phases are separated, the organic phase is dried and evaporated, and the product is purified by crystallization and/ or chromatography.

EXAMPLE 1

A liquid-crystalline phase comprising
18% of 4-(5-Heptylpyrimidin-2-yl)-phenyl p-pentylbenzyl ether,
26% of 4-(5-Heptylpyrimidin-2-yl)-phenyl p-hexylbenzyl ether,
13% of 4-(5-Nonylpyrimidin-2-yl)-phenyl p-pentylbenzyl ether,
4% of 4-(5-Nonylpyrimidin-2-yl)-phenyl p-hexylbenzyl ether,
24% of 2-p-Nonyloxyphenyl-5-nonylpyrimidine,
8% of p-(5-Nonylpyrimidin-2-yl)-phenyl p-(5-pentylpyri midin-2-yl)-benzoate and
7% of p-(5-Heptylpyrimidin-2-yl)-phenyl p-(5-heptyl pyrimidin-2-yl)-benzoate
has $C/S_c$ 13°, $S_c/N$ 64° and N/I 124°.

EXAMPLE 2

A liquid-crystalline phase comprising
18% of 4-(5-Heptylpyrimidin-2-yl)-phenyl p-pentylbenzyl ether,
22% of 4-(5-Heptylpyrimidin-2-yl)-phenyl p-hexylbenzyl ether,
13% of 4-(5-Nonylpyrimidin-2-yl)-phenyl p-pentylbenzyl ether,
10% of 4-(5-Nonylpyrimidin-2-yl)-phenyl p-hexylbenzyl ether,
21% of 2-p-Undecyloxyphenyl-5-heptylpyrimidine, of 2-(p-Pentylphenyl)-pyrimidin-5-yl p-octylbenzyl ether,
5% of 2-(p-Hexylphenyl)-pyrimidin-5-yl p-nonylbenzyl ether and
6% of 4-(5-Octylpyrimidin-2-yl)-phenyl trans-4-pentyl cyclohexylmethyl ether
has $C/S_c$ 6°, $S_c/N$ 63.5° and N/I 96°.

EXAMPLE 3

A liquid-crystalline phase comprising
12% of 4-(5-Heptylpyrimidin-2-yl)-phenyl p-pentylbenzyl ether,
15% of 4-(5-Heptylpyrimidin-2-yl)-phenyl p-hexylbenzyl ether,
10% of 4-(5-Nonylpyrimidin-2-yl)-phenyl p-hexylbenzyl ether,
8% of 2-p-Nonyloxyphenyl-5-nonylpyrimidine,
16% of 2-p-Decyloxyphenyl-5-octylpyrimidine,
13% of p-(5-Hexylpyrimidin-2-yl)-phenyl p-(5-pentylpyrimidin-2-yl)-benzoate,
12% of 2-(p-Pentylphenyl)-pyrimidin-2-yl p-nonylbenzyl ether,
5% of 2-p-Undecyloxyphenyl-5-heptylpyrimidine,
4% of 4-(5-Octylpyrimidin-2-yl)-phenyl trans-4-hexylcyclo-hexylmethyl ether and
5% of 4-(5-Nonylpyrimidin-2-yl)-phenyl trans-4-pentylcyclohexylmethyl ether
has $C/S_c$ −1°, $S_c/N$ 63° and N/I 94°.

EXAMPLE 4

A liquid-crystalline phase comprising
20% of 4-(5-Hexylpyrimidin-2-yl)-phenyl p-hexylbenzyl ether,
15% of 4-(5-Heptylpyrimidin-2-yl)-phenyl p-pentylbenzyl ether,
10% of 4-(5-Nonylpyrimidin-2-yl)-phenyl p-hexylbenzyl ether,
4% of 4-(5-Heptylpyrimidin-2-yl)-phenyl p-hexylbenzyl ether,
16% of 4-(5-Nonylpyrimidin-2-yl)-phenyl p-pentylbenzyl ether,
10% of 2-p-Nonyloxyphenyl-5-heptylpyrimidine,
7% of 2-p-Nonyloxyphenyl-5-nonylpyrimidine,
8% of p-Hexyloxyphenyl trans-4-pentylcyclohexanecarboxylate and
10% of p-Heptylphenyl p-decyloxybenzoate
has $C/s_c$ 0°, $S_c/N$ 79° and N/I 87°.

EXAMPLE 5

A liquid-crystalline phase comprising
18% of 4-(5-Hexylpyrimidin-2-yl)-phenyl p-hexylbenzyl ether,
14% of 4-(5-Heptylpyrimidin-2-yl)-phenyl p-pentylbenzyl ether,
10% of 4-(5-Hexylpyrimidin-2-yl)-phenyl p-pentylbenzyl ether,
10% of 4-(5-Nonylpyrimidin-2-yl)-phenyl p-hexylbenzyl ether,
20% of 4-(5-Heptylpyrimidin-2-yl)-phenyl p-hexylbenzyl ether,
10% of 4-(5-Nonylpyrimidin-2-yl)-phenyl p-pentylbenzyl ether,
6% of 2-p-Decyloxyphenyl-5-octylpyrimidine,
7% of p-Heptylphenyl p-decyloxybenzoate and
5% of p-Butyloxyphenyl p-(p-decyloxybenzoyloxy)-benzoate
has $C/S_c$ 12°, $S_c/N$ 96° and $N/I$ 107°.

EXAMPLE 6

A liquid-crystalline phase comprising
27% of 4-(5-Hexylpyrimidin-2-yl)-phenyl p-hexylbenzyl ether,
14% of 4-(5-Heptylpyrimidin-2-yl)-phenyl p-pentylbenzyl ether,
7% of 4-(5-Hexylpyrimidin-2-yl)-phenyl p-pentylbenzyl ether,
2% of 4-(5-Nonylpyrimidin-2-yl)-phenyl p-hexylbenzyl ether,
18% of 4-(5-Heptylpyrimidin-2-yl)-phenyl p-hexylbenzyl ether,
7% of 4-(5-Nonylpyrimidin-2-yl)-phenyl p-pentylbenzyl ether,
4% of 2-p-Heptyloxyphenyl-5-octylpyrimidine,
2% of p-Hexyloxyphenyl trans-4-pentylcyclohexanecarboxylate,
10% of 4'-Pentylbiphenyl-4-yl p-pentylbenzoate and
9% of 4'-Pentylbiphenyl-4-yl p-hexylbenzoate
has $C/S_c$ 9°, $S_c/N$ 82° and $N/I$ 116°.

EXAMPLE 7

A liquid-rystalline phase comprising
16% of 4-(5-Hexylpyrimidin-2-yl)-phenyl p-pentylbenzyl ether,
26% of 4-(5-Heptylpyrimidin-2-yl)-phenyl p-pentylbenzyl ether,
36% of 4-(5-Heptylpyrimidin-2-yl)-phenyl p-hexylbenzyl ether,
18% of 4-(5-Nonylpyrimidin-2-yl)-phenyl p-pentylbenzyl ether and
4% of 4-(5-Nonylpyrimidin-2-yl)-phenyl p-hexylbenzyl ether
has $C/S_c$ 8°, $S_c/N$ 84.5° and $N/I$ 104°.

EXAMPLE 8

A liquid-crystalline phase comprising
30% of 4-(5-Hexylpyrimidin-2-yl)-phenyl p-hexylbenzyl ether,
15% of 4-(5-Heptylpyrimidin-2-yl)-phenyl p-pentylbenzyl ether,
8% of 4-(5-Hexylpyrimidin-2-yl)-phenyl p-pentylbenzyl ether,
2% of 4-(5-Nonylpyrimidin-2-yl)-phenyl p-hexylbenzyl ether,
21% of 4-(5-Heptylpyrimidin-2-yl)-phenyl p-hexylbenzyl ether,
8% of 4-(5-Nonylpyrimidin-2-yl)-phenyl p-pentylbenzyl ether and
16% of 2-p-Nonyloxyphenyl-5-nonylpyrimidine
has $C/S_c$ −5°, $S_c/N$ 81° and $N/I$ 99°.

EXAMPLE 9

A liquid-crystalline phase comprising
27% of 4-(5-Hexylpyrimidin-2-yl)-phenyl p-hexylbenzyl ether,
14% of 4-(5-Heptylpyrimidin-2-yl)-phenyl p-pentylbenzyl ether,
7% of 4-(5-Hexylpyrimidin-2-yl)-phenyl p-pentylbenzyl ether,
2% of 4-(5-Nonylpyrimidin-2-yl)-phenyl p-hexylbenzyl ether,
18% of 4-(5-Heptylpyrimidin-2-yl)-phenyl p-hexylbenzyl ether,
7% of 4-(5-Nonylpyrimidin-2-yl)-phenyl p-pentylbenzyl ether,
14% of 2-p-Nonyloxyphenyl-5-nonylpyrimidine and
10% of R-4-(5-Hexylpyrimidin-2-yl)-phenyl 2-chloropropionate
has $C/S^*_c$ −4°, $S^*_c/Ch$ 64.7° and $Ch/I$ 92.5°.

The values of the spontaneous polarization (nC/cm$^2$) and the pitch height (μm) of this phase are given for various temperatures in the following table:

| Temperature [°C.] | Spontaneous polarization | Pitch |
|---|---|---|
| 60 | 2.4 | 14 |
| 50 | 4.9 | 13.5 |
| 40 | 6.1 | 12 |
| 20 | 7.3 | 11 |
| 8 | 9.0 | 10 |

EXAMPLE 10

A liquid-crystalline phase comprising
31% of 2-p-Nonyloxyphenyl-5-nonylpyrimidine
9% of 2-p-Decyloxyphenyl-5-octylpyrimidine
14% of 2-p-Octyloxyphenyl-5-octylpyrimidine
18% of 2-p-Nonyloxyphenyl-5-heptylpyrimidine
13% of 2-p-Heptyloxyphenyl-5-heptylpyrimidine
10% of 4-(5-Octylpyrimidin-2-yl)-phenyl 2-fluoro-4-decyloxybenzoate and
5% of 4-(5-Decylpyrimidin-2-yl)-phenyl 2-fluoro-4-hexyloxybenzoate
has $C/S_c$ 7°, $S_c/S_A$ 57°, $S_A/N$ 67°, $N/I$ 70.5°.

EXAMPLE 11

A liquid-crystalline phase comprising
28% of 2-p-Nonyloxyphenyl-5-nonylpyrimidine
3% of 2-p-Nonyloxyphenyl-5-octylpyrimidine
25% of 2-p-Heptyloxyphenyl-5-octylpyrimidine
10% of 2-p-Heptyloxy-5-heptylpyrimidine
5% of 2-p-Decyloxy-5-heptylpyrimidine
9% of 4-(5-Octylpyrimidin-2-yl)-phenyl 2-fluoro-4-decyloxybenzoate
10% of 4-(5-Heptylpyrimidin-2-yl)-phenyl 3-fluo.o-4-heptyloxybenzoate and
10of 2-Fluoro-4-nonylphenyl 4-(5-decylpyrimidin-2-yl)-benzoate
has $C/S_c$ 13°, $S_c/S_A$ 64°, $S_A/N$ 68°, $N/I$ 83°.

EXAMPLE 12

A liquid-crystalline phase comprising
30% of 2-p-Nonyloxyphenyl-5-nonylpyrimidine 15% of 2-p-Decyloxyphenyl-5-octylpyrimidine
15% of 2-p-Octyloxyphenyl-5-octylpyrimidine
12% of 2-p-Nonyloxyphenyl-5-heptylpyrimidine
10% of 3-Fluoro-4-hexylphenyl 4-(5-octylpyrimidin-2-yl)-benzoate
3% of 2-Cyano-4-decylphenyl 4-(5-decylpyrimidin-2-yl)-benzoate
6% of 2-(4-Heptylphenyl)-pyrimidin-5-yl 2-fluoro-4-heptyl-benzoate and
9% of 2-(4-Octylphenyl)-pyrimidin-5-yl 3-fluoro-4-hexylbenzoate
has $C/S_c$ 16°, $S_c/S_A$ 59°, $S_A/N$ 63°, $N/I$ 79°.

EXAMPLE 13

A liquid-crystalline phase comprising
30% of 2-p-Nonyloxyphenyl-5-nonylpyrimidine
15% of 2-p-Decyloxyphenyl-5-octylpyrimidine
20% of 2-p-Octyloxyphenyl-5-octylpyrimidine
15% of 2-p-Nonyloxyphenyl-5-heptylpyrimidine
10% of 2-p-Heptyloxyphenyl-5-heptylpyrimidine and
10% of 2-Fluoro-4-(5-octylpyrimidin-2-yl)-phenyl 4-octylbenzoate
has $C/S_c$ 4°, $S_c/S_A$ 22°, $S_A/N$ 65°, $N/I$ 74°.

EXAMPLE 14

A liquid-crystalline phase comprising
33% of 4-(5-Hexylpyrimidin-2-yl)-phenyl p-hexylbenzyl ether
15% of 4-(5-Heptylpyrimidin-2-yl)-phenyl p-pentylbenzyl ether
10% of 4-(5-Hexylpyrimidin-2-yl)-phenyl p-pentylbenzyl ether
3% of 4-(5-Nonylpyrimidin-2-yl)-phenyl p-hexylbenzyl ether
24% of 4-(5-Heptylpyrimidin-2-yl)-phenyl p-hexylbenzyl ether
10% of 4-(5-Octylpyrimidin-2-yl)-phenyl 2-fluoro-4-heptyloxybenzoate and
5% of 3-Fluoro-4-octylphenyl 4-(5-decylpyrimidin-2-yl)-benzoate
has $C/S_c$ 3°, $S_c/N$ 75°, $N/I$ 98°.

EXAMPLE 15

A liquid-crystalline phase comprising
32% of 4-(5-Hexylpyrimidin-2-yl)-phenyl p-hexylbenzyl ether
16% of 4-(5-Heptylpyrimidin-2-yl)-phenyl p-pentylbenzyl ether
9% of 4-(5-Hexylpyrimidin-2-yl)-phenyl p-pentylbenzyl ether
2% of 4-(5-Nonylpyrimidin-2-yl)-phenyl p-hexylbenzyl ether
18% of 4-(5-Nonylpyrimidin-2-yl)-phenyl p-pentylbenzyl ether
13% of 4-(5-Heptylpyrimidin-2-yl)-phenyl 3-fluoro-4-heptyl oxybenzoate
5% of 2-Fluoro-4-nonylphenyl 4-(5-decylpyrimidin-2-yl) benzoate and
5% of 2-Cyano-4-octylphenyl 4-(5-Nonylpyrimidin-2-yl) benzoate
has $C/S_c$ −1°, $S_c/N$ 77°, $N/I$ 94°.

EXAMPLE 16

A liquid-crystalline phase comprising
17% of 4-(5-Heptylpyrimidin-2-yl)-phenyl p-pentylbenzyl ether
25% of 4-(5-Heptylpyrimidin-2-yl)-phenyl p-hexylbenzyl ether
13% of 4-(Nonylpyrimidin-2-yl)-phenyl p-pentylbenzyl ether
4% of 4-(Nonylpyrimidin-2-yl)-phenyl p-hexylbenzyl ether
11% of 2-(4-Nonylphenyl)-pyrimidin-5-yl) 2-fluoro-4-heptyl benzoate
10% of 2-Fluoro-4-(5-decylpyrimidin-2-yl)-pheny 4-octyl benzoate
15% of 4-(5-Heptylpyrimidin-2-yl)-phenyl 2-fluoro-4-heptyl oxybenzoate and
5% of 2-Fluoro-4-nonylphenyl 4-(5-nonylpyrimidin-2-yl) benzoate
has $C/S_c$ 5°, $S_c/N$ 75°, $N/I$ 97°.

EXAMPLE 17

A liquid-crystalline phase comprising
33% of 4-(5-Hexylpyrimidin-2-yl)-phenyl p-hexylbenzyl ether
18% of 4-(5-Heptylpyrimidin-2-yl)-phenyl p-pentylbenzyl ether
10% of 4-(5-Hexylpyrimidin-2-yl)-phenyl p-pentylbenzyl ether
3% of 4-(5-Nonylpyrimidin-2-yl)-phenyl p-hexylbenzyl ether
25% of 4-(5-Heptylpyrimidin-2-yl)-phenyl p-hexylbenzyl ether
4% of 5-(4-Octylphenyl)-pyrimidin-2-yl 3-fluoro-4-octyl benzoate and
7% of 2-Fluoro-4-(5-decylpyrimidin-2-yl)-phenyl 4-heptyl benzoate
has $C/S_c$ 10°, $S_c/N$ 77°, $N/I$ 100°.

EXAMPLE 18

A mixture of 0.65 g of 5-methoxy-2-(4-n-octylphenyl)-pyrimidine [can be obtained by condensation of methyl β-hydroxy-α-methoxyacrylate with 4-n-octylbenzamidine hydrochloride, reaction of the 4-hydroxy-5-methoxypyrimidine obtained with P2S5 and reduction of the 4-mercaptopyrimidine obtained with a Raney nickel according to J. H. Chesterfield et al., J. Chem. Soc. 4590 (1960)] and 1.0 g of KOH in 15 ml of ethylene glycol are boiled for 10 hours. 10 ml of water are added to the cooled solution, which is then acidified using glacial acetic acid and extracted five times with ether. After conventional work-up, 5-hydroxy-2-(4-n-octylphenyl)-pyrimidine is obtained. (The other homologues can be obtained analogously). 0.26 g of the 5-hydroxy-2-(4-n-octylphenyl)pyrimidine obtained, 0.25 g of 4-n-heptylbenzoyl chloride and 0.15 g of potassium carbonate in 2.5 ml of dimethylformamide are subsequently heated at 100° C. for 12 hours with stirring. The salt is removed by filtration under suction, and the filtrate is concentrated to a residue, which is taken up in ether and washed with water until neutral. Conventional work-up gives 2-(4-n-octylphenyl)-pyrimidin-5-yl 4-n-heptylbenzoate.

The following are prepared analogously:
2-(4-Propylphenyl)-pyrimidin-5-yl 4-propylbenzoate 2-(4-Pentylphenyl)-pyrimidin-5-yl 4-propylbenzoate
2-(4-Hexylphenyl)-pyrimidin-5-yl 4-propylbenzoate
2-(4-Heptylphenyl)-pyrimidin-5-yl 4-propylbenzoate
2-(4-Octylphenyl)-pyrimidin-5-yl 4-propylbenzoate
2-(4-Nonylphenyl)-pyrimidin-5-yl 4-propylbenzoate
2-(4-Decylphenyl)-pyrimidin-5-yl 4-propylbenzoate
2-(4-Propylphenyl)-pyrimidin-5-yl 4-hexylbenzoate
2-(4-Pentylphenyl)-pyrimidin-5-yl 4-hexylbenzoate
2-(4-Hexylphenyl)-pyrimidin-5-yl 4-hexylbenzoate
2-(4-Heptylpenyl)-pyrimidin-5-yl 4-hexylbenzoate
2-(4-Octylphenyl)-pyrimidin-5-yl 4-hexylbenzoate
2-(4-Nonylphenyl)-pyrimidin-5-yl 4-hexylbenzoate
2-(4-Decylphenyl)-pyrimidin-5-yl 4-hexylbenzoate
2-(4-Propylphenyl)-pyrimidin-5-yl 4-heptylbenzoate
2-(4-Pentylphenyl)-pyrimidin-5-yl 4-heptylbenzoate
2-(4-Hexylphenyl)-pyrimidin-5-yl 4-heptylbenzoate
2-(4-Heptylphenyl)-pyrimidin-5-yl 4-heptylbenzoate
2-(4-Octylphenyl)-pyrimidin-5-yl 4-heptylbenzoate
2-(4-Nonylphenyl)-pyrimidin-5-yl 4-heptylbenzoate
2-(4-Decylphenyl)-pyrimidin-5-yl 4-heptylbenzoate
2-(4-Propylphenyl)-pyrimidin-5-yl 4-octylbenzoate
2-(4-Pentylphenyl)-pyrimidin-5-yl 4-octylbenzoate
2-(4-Hexylphenyl)-pyrimidin-5-yl 4-octylbenzoate
2-(4-Heptylphenyl)-pyrimidin-5-yl 4-octylbenzoate
2-(4-Octylphenyl)-pyrimidin-5-yl 4-octylbenzoate
2-(4-Nonylphenyl)-pyrimidin-5-yl 4-octylbenzoate
2-(4-Decylphenyl)-pyrimidin-5-yl 4-octylbenzoate
2-(4-Propylphenyl)-pyrimidin-5-yl 4-nonylbenzoate
2-(4-Pentylphenyl)-pyrimidin-5-yl 4-nonylbenzoate
2-(4-Hexylphenyl)-pyrimidin-5-yl 4-nonylbenzoate
2-(4-Heptylphenyl)-pyrimidin-5-yl 4-nonylbenzoate
2-(4-Octylphenyl)-pyrimidin-5-yl 4-nonylbenzoate
2-(4-Nonylphenyl)-pyrimidin-5-yl 4-nonylbenzoate
2-(4-Decylphenyl)-pyrimidin-5-yl 4-nonylbenzoate
2-(4-Propylphenyl)-pyrimidin-5-yl 4-decylbenzoate
2-(4-Pentylphenyl)-pyrimidin-5-yl 4-decylbenzoate
2-(4-Hexylphenyl)-pyrimidin-5-yl 4-decylbenzoate
2-(4-Heptylphenyl)-pyrimidin-5-yl 4-decylbenzoate
2-(4-Octylphenyl)-pyrimidin-5-yl 4-decylbenzoate
2-(4-Nonylphenyl)-pyrimidin-5-yl 4-decylbenzoate
2-(4-Decylphenyl)-pyrimidin-5-yl 4-decylbenzoate

EXAMPLE 19

A mixture of 10.2 g of 5-hydroxy-2-(4-n-hexylphenyl)-pyrimidine, 8.6 g of 4-n-propylbenzyl bromide, 8.6 g of potassium carbonate and 50 ml of dimethylformamide are warmed at 90° for 10 hours. Conventional work-up gives 2-(4-n-hexylphenyl)-pyrimidin-5-yl p-n-propylbenzyl ether.

The following are prepared analogously:
2-(4-Butylphenyl)-pyrimidin-5-yl p-propylbenzyl ether
2-(4-Butylphenyl)-pyrimidin-5-yl p-pentylbenzyl ether
2-(4-Butylphenyl)-pyrimidin-5-yl p-hexylbenzyl ether
2-(4-Butylphenyl)-pyrimidin-5-yl p-heptylbenzyl ether
2-(4-Butylphenyl)-pyrimidin-5-yl p-octylbenzyl ether
2-(4-Butylphenyl)-pyrimidin-5-yl p-nonylbenzyl ether
2-(4-Butylphenyl)-pyrimidin-5-yl p-decylbenzyl ether
2-(4-Pentylphenyl)-pyrimidin-5-yl p-propylbenzyl ether
2-(4-Pentylphenyl)-pyrimidin-5-yl p-pentylbenzyl ether
2-(4-Pentylphenyl)-pyrimidin-5-yl p-hexylbenzyl ether
2-(4-Pentylphenyl)-pyrimidin-5-yl p-heptylbenzyl ether
2-(4-Pentylphenyl)-pyrimidin-5-yl p-octylbenzyl ether
2-(4-Pentylphenyl)-pyrimidin-5-yl p-nonylbenzyl ether
2-(4-Pentylphenyl)-pyrimidin-5-yl p-decylbenzyl ether
2-(4-Hexylphenyl)-pyrimidin-5-yl p-propylbenzyl ether
2-(4-Hexylphenyl)-pyrimidin-5-yl p-pentylbenzyl ether
2-(4-Hexylphenyl)-pyrimidin-5-yl p-hexylbenzyl ether
2-(4-Hexylphenyl)-pyrimidin-5-yl p-heptylbenzyl ether
2-(4-Hexylphenyl)-pyrimidin-5-yl p-octylbenzyl ether
2-(4-Hexylphenyl)-pyrimidin-5-yl p-nonylbenzyl ether
2-(4-Hexylphenyl)-pyrimidin-5-yl p-decylbenzyl ether
2-(4-Heptylphenyl)-pyrimidin-5-yl p-propylbenzyl ether
2-(4-Heptylphenyl)-pyrimidin-5-yl p-pentylbenzyl ether
2-(4-Heptylphenyl)-pyrimidin-5-yl p-hexylbenzyl ether
2-(4-Heptylphenyl)-pyrimidin-5-yl p-heptylbenzyl ether
2-(4-Heptylphenyl)-pyrimidin-5-yl p-octylbenzyl ether
2-(4-Heptylphenyl)-pyrimidin-5-yl p-nonylbenzyl ether
2-(4-Heptylphenyl)-pyrimidin-5-yl p-decylbenzyl ether
2-(4-Octylphenyl)-pyrimidin-5-yl p-propylbenzyl ether
2-(4-Octylphenyl)-pyrimidin-5-yl p-pentylbenzyl ether
2-(4-Octylphenyl)-pyrimidin-5-yl p-hexylbenzyl ether
2-(4-Octylphenyl)-pyrimidin-5-yl p-heptylbenzyl ether
2-(4-Octylphenyl)-pyrimidin-5-yl p-octylbenzyl ether
2-(4-Octylphenyl)-pyrimidin-5-yl p-nonylbenzyl ether
2-(4-Octylphenyl)-pyrimidin-5-yl p-decylbenzyl ether
2-(4-Nonylphenyl)-pyrimidin-5-yl p-propylbenzyl ether
2-(4-Nonylphenyl)-pyrimidin-5-yl p-pentylbenzyl ether
2-(4-Nonylphenyl)-pyrimidin-5-yl p-hexylbenzyl ether
2-( 4-Nonylphenyl)-pyrimidin-5-yl p-heptylbenzyl ether
2-(4-Nonylphenyl)-pyrimidin-5-yl p-heptylbenzyl ether
2-(4-Nonylphenyl)-pyrimidin-5-yl p-octylbenzyl ether
2-(4-Nonylphenyl)-pyrimidin-5-yl p-nonylbenzyl ether
2-(4-Nonylphenyl)-pyrimidin-5-yl p-decylbenzyl ether
2-(4-Nonylphenyl)-pyrimidin-5-yl p-propylbenzyl ether
2-(4-Nonylphenyl)-pyrimidin-5-yl p-pentylbenzyl ether
2-(4-Nonylphenyl)-pyrimidin-5-yl p-hexylbenzyl ether
2-(4-Nonylphenyl)-pyrimidin-5-yl p-heptylbenzyl ether
2-(4-Nonylphenyl)-pyrimidin-5-yl p-octylbenzyl ether
2-(4-Nonylphenyl)-pyrimidin-5-yl p-nonylbenzyl ether
2-(4-Nonylphenyl)-pyrimidin-5-yl p-decylbenzyl ether

EXAMPLE 20

14.2 g of 4-(5-hexylpyrimidin-2-yl)-benzoic acid (can be obtained from 4-(5-hexylpyrimidin-2-yl)-benzonitrile by saponification) are refluxed with 10 g of thionyl chloride in 120 ml of toluene until hydrogen chloride evolution ceases. The mixture is freed of volatile components under reduced pressure. The residue is taken up in 180 ml of dichloromethane, and 10 ml of triethylamine and 14.2 g of 4-(5-octylpyrimidin-2-yl)-phenol (can be obtained from 4-hydroxybenzamidine hydrochloride and methyl α-octyl-β-hydroxyacrylate) are added. After stirring for 20 hours at 20°, the precipitated triethylammonium chloride is filtered off and the filtrate is concentrated. 4-(5-Octylpyrimidin-2-yl)-phenyl 4-(5-hexylpyrimidin-2-yl)-benzoate crystallizes.

The following are prepared analogously to this:
4-(5-Propylpyrimidin-2-yl)-phenyl 4-(5-propylpyrimidin-2-yl)-benzoate
4-(5-Pentylpyrimidin-2-yl)-phenyl 4-(5-propylpyrimidin-2-yl)-benzoate
4-(5-Hexylpyrimidin-2-yl)-phenyl 4-(5-propylpyrimidin-2-yl)-benzoate
4-(5-Heptylpyrimidin-2-yl)-phenyl 4-(5-propylpyrimidin-2-yl)-benzoate
4-(5-Octylpyrimidin-2-yl)-phenyl 4-(5-propylDyrimidin-2-yl)-benzoate
4-(5-Nonylpyrimidin-2-yl)-phenyl 4-(5-propylpyrimidin-2-yl)-benzoate
4-(5-Decylpyrimidin-2-yl)-phenyl 4-(5-propylpyrimidin-2-yl)-benzoate
4-(5-Propylpyrimidin-2-yl)-phenyl 4-(5-pentylpyrimidin-2-yl)-benzoate
4-(5-Pentylpyrimidin-2-yl)-phenyl 4-(5-pentylpyrimidin-2-yl)-benzoate 4-(5-Hexylpyrimidin-2-yl)-phenyl 4-(5-pentylpyrimidin-2-yl)-benzoate
4-(5-Heptylpyrimidin-2-yl)-phenyl 4-(5-pentylpyrimidin-2-yl)-benzoate
4-(5-Octylpyrimidin-2-yl)-phenyl 4-(5-pentylpyrimidin-2-yl)-benzoate
4-(5-Nonylpyrimidin-2-yl)-phenyl 4-(5-pentylpyrimidin-2-yl)-benzoate
4-(5-Decylpyrimidin-2-yl)-phenyl 4-(5-pentylpyrimidin-2-yl)-benzoate
4-(5-Propylpyrimidin-2-yl)-phenyl 4-(5-hexylpyrimidin-2-yl)-benzoate
4-(5-Pentylpyrimidin-2-yl)-phenyl 4-(5-hexylpyrimidin-2-yl)-benzoate
4-(5-Hexylpyrimidin-2-yl)-phenyl 4-(5-hexylpyrimidin-2-yl)-benzoate
4-(5-Heptylpyrimidin-2-yl)-phenyl 4-(5-hexylpyrimidin-2-yl)-benzoate
4-(5-Octylpyrimidin-2-yl)-phenyl 4-(5-hexylpyrimidin-2-yl)-benzoate
4-(5-Nonylpyrimidin-2-yl)-phenyl 4-(5-hexylpyrimidin-2-yl)-benzoate
4-(5-Decylpyrimidin-2-yl)-phenyl 4-(5-hexylpyrimidin-2-yl)-benzoate
4-(5-Propylpyrimidin-2-yl)-phenyl 4-(5-heptylpyrimidin-2-yl)-benzoate
4-(5-Pentylpyrimidin-2-yl)-phenyl 4-(5-heptylpyrimidin-2-yl)-benzoate
4-(5-Hexylpyrimidin-2-yl)-phenyl 4-(5-heptylpyrimidin-2-yl)-benzoate, melting point 97°, boiling point 276°
4-(5-Heptylpyrimidin-2-yl)-phenyl 4-(5-heptylpyrimidin-2-yl)-benzoate
4-(5-Octylpyrimidin-2-yl)-phenyl 4-(5-heptylpyrimidin-2-yl)-benzoate
4-(5-Nonylpyrimidin-2-yl)-phenyl 4-(5-heptylpyrimidin-2-yl)-benzoate
4-(5-Decylpyrimidin-2-yl)-phenyl 4-(5-heptylpyrimidin-2-yl)-benzoate
4-(5-Propylpyrimidin-2-yl)-phenyl 4-(5-octylpyrimidin-2-yl)-benzoate
4-(5-Pentylpyrimidin-2-yl)-phenyl 4-(5-octylpyrimidin-2-yl)-benzoate
4-(5-Hexylpyrimidin-2-yl)-phenyl 4-(5-octylpyrimidin-2-yl)-benzoate
4-(5-Heptylpyrimidin-2-yl)-pheqyl 4-(5-octylpyrimidin-2-yl)-benzoate
4-(5-Octylpyrimidin-2-yl)-phenyl 4-(5-octylpyrimidin-2-yl)-benzoate
4-(5-Nonylpyrimidin-2-yl)-phenyl 4-(5-octylpyrimidin-2-yl)-benzoate
4-(5-Decylpyrimidin-2-yl)-phenyl 4-(5-octylpyrimidin-2-yl)-benzoate
4-(5-Propylpyrimidin-2-yl)-phenyl 4-(5-nonylpyrimidin-2-yl)-benzoate
4-(5-Pentylpyrimidin-2-yl)-phenyl 4-(5-nonylpyrimidin-2-yl)-benzoate
4-(5-Hexylpyrimidin-2-yl)-phenyl 4-(5-nonylpyrimidin-2-yl)-benzoate
4-(5-Heptylpyrimidin-2-yl)-phenyl 4-(5-nonylpyrimidin-2-yl)-benzoate
4-(5-Octylpyrimidin-2-yl)-phenyl 4-(5-nonylpyrimidin-2-yl)-benzoate
4-(5-Nonylpyrimidin-2-yl)-phenyl 4-(5-nonylpyrimidin-2-yl)-benzoate
4-(5-Decylpyrimidin-2-yl)-phenyl 4-(5-nonylpyrimidin-2-yl)-benzoate
4-(5-Propylpyrimidin-2-yl)-phenyl 4-(5-decylpyrimidin-2-yl)-benzoate
4-(5-Pentylpyrimidin-2-yl)-phenyl 4-(5-decylpyrimidin-2-yl)-benzoate
4-(5-Hexylpyrimidin-2-yl)-phenyl 4-(5-decylpyrimidin-2-yl)-benzoate
4-(5-Heptylpyrimidin-2-yl)-phenyl 4-(5-decylpyrimidin-2-yl)-benzoate
4-(5-Octylpyrimidin-2-yl)-phenyl 4-(5-decylpyrimidin-2-yl)-benzoate
4-(5-Nonylpyrimidin-2-yl)-phenyl 4-(5-decylpyrimidin-2-yl)-benzoate
4-(5-Decylpyrimidin-2-yl)-phenyl 4-(5-decylpyrimidin-2-yl)-benzoate

EXAMPLE 21

A liquid-crystalline phase comprising
11% of p-(5-Heptylpyrimidin-2-yl)-phenyl p-pentylbenzyl ether,
15% of p-(5-Heptylpyrimidin-2-yl)-phenyl p-hexylbenzyl ether,
18% of p-(5-Nonylpyrimidin-2-yl)-phenyl p-pentylbenzyl ether,
14% of p-(5-Nonylpyrimidin-2-yl)-phenyl p-heptylbenzyl ether,
23% of 2-p-Nonyloxyphenyl-5-nonylpyrimidine,
5% of 4-(5-Heptylpyrimidin-2-yl)-phenyl p-hexyloxybenzoate,
4% of 4-(5-Octylpyrimidin-2-yl)-phenyl p-octyloxy-m-fluorobenzoate and
10% of R-4-(5-Hexylpyrimidin-2-yl)-phenyl 2-chloropropionate
exhibits C 4° $S_c^*$ 76° Ch 95° I.

EXAMPLE 22

A liquid-crystalline phase comprising
3% of 2-p-Hexyloxyphenyl-5-heptylpyrimidine,
3% of 2-p-Heptyloxyphenyl-5-heptylpyrimidine,
3% of 2-p-Octyloxyphenyl-5-heptylpyrimidine,
3% of 2-p-Nonyloxyphenyl-5-heptylpyrimidine
6% of 2-p-Hexyloxyphenyl-5-nonylpyrimidine,
15% of 2-p-Nonyloxyphenyl-5-nonylpyrimidine,
16% of 1(p-Hexylphenyl)-2-(p-(5-heptylpyrimidin-2-yl)-phenyl)-ethane,
19% of 1-(p-Octyl-m-fluorophenyl)-2-(p-(5-octylpyrimidin-2-yl)-phenyl)-ethane,
15% of optically active 4-(5-nonylpyrimidin-2-yl)-phenyl-3-chloro-4-(2-octyloxy)-benzoate and
17% of optically active 1-p-(2-octyloxycarbonyl)-phenyl-2-(p-(5-heptylpyrimidin-2-yl)-phenyl)-ethane
exhibits C 9° $S_c^*$ 74° Ch 89° I

EXAMPLE 23

A liquid-crystalline phase comprising
4% of 2-p-Heptyloxyphenyl-5-octylpyrimidine,
4% of 2-p-Octyloxyphenyl-5-octylpyrimidine,
4% of 2-p-Nonyloxyphenyl-5-octylpyrimidine,
16% of p-(5-Nonylpyrimidin-2-yl)-phenyl p-pentylbenzyl ether,
11% of p-(5-Nonylpyrimidin-2-yl)-phenyl p-heptylbenzyl ether,
13% of 5-(p-Octylphenyl)-pyrimidin-2-yl p-octyloxybenzoate,
16% of 5-(p-Heptylphenyl)-pyrimidin-2-yl p-hexyloxybenzoate,
11% of 5-(p-Octylphenyl)-pyrimidin-2-yl p-heptyloxy-m-fluorobenzoate and
21% of 2-p-Nonyloxyphenyl-5-pyrimidine
exhibits C 5° $S_c$.

EXAMPLE 24

A liquid-crystalline phase comprising
11% of p-(5-Heptylpyrimidin-2-yl)-phenyl p-pentylbenzyl ether,
9% of p-(5-Heptylpyrimidin-2-yl)-phenyl p-hexylbenzyl ether,
12% of p-(5-Nonylpyrimidin-2-yl)-phenyl p-pentylbenzyl ether,
10% of p-(5-Nonylpyrimidin-2-yl)-phenyl p-heptylbenzyl ether,
20% of 2-p-Nonyloxyphenyl-5nonylpyrimidine,
9% of 1-(trans-4-Heptylcyclohexyl)-2-(p-(5-octylpyrimidin-2-yl)-phenyl)-ethane,
8% of 1-(trans-4-Octylcyclohexyl)-2-(p-5nonylpyrimidin-2yl)-phenyl ethane,m
10% of optically active 1-(p-(2-Octyloxycarbonyl)-phenyl)-2-(p-)5-heptylpyrimidin-2-yl)-phenyl)-ethane and
11% of 1-(p-Heptyloxy-m-fluorophenyl)-2-(p-(5-heptylpyrimidin-2yl)-phenyl)-ethane,
exhibits C 3° $S_c$* 72° Ch 93° I.

EXAMPLE 25

A liquid-crystalline phase comprising
3% of 2-p-Heptyloxyphenyl-5heptylpyrimidine,
3% of 2-p-Octyloxyphenyl-5-heptylpyrimidine,
7% of p-(4-Heptylpyrimidin-2-yl)-phenyl p-pentylbenzyl ether,
5% of p-(5-Heptylpyrimidin-2-yl)-phenyl p-hexylbenzyl ether,
20% of 2-p-Nonyloxyphenyl-5-nonylpyrimidine,
10% of R-4-(5-Hexylpyrimidin-2-yl)-phenyl 2-chloropropionate,
8% 1-(p-Hexylphenyl)-2-(p-5-heptylpyrimidin-2-yl)-phenyl)-ethane
13% of 1-(p-Octylphenyl)-2-(p-5-heptylpyrimidin-2-yl)-phenyl)-ethane,
11% of 1-(p-Heptylphenyl)-2-(p-(5-nonylpyrimidin-2-yl)-phenyl)-ethane and
9% of 1-(p-Octylphenyl)-2-(p-(5-nonylpyrimidin-2-yl)-phenyl)-ethane
exhibits C 8° $S_c$* 74° Ch 88° I.

EXAMPLE 26

A liquid-crystalline phase comprising
3% of 2-p-Hexyloxyphenyl-5-heptylpyrimidine,
3% of 2-p-Heptyloxyphenyl-5-heptylpyrimidine,
3% of 2-p-Octyloxyphenyl-5-heptylpyrimidine,
3% of 2-p-Nonyloxyphenyl-5-heptylpyrimidine,
6% of 2-p-Hexyloxyphenyl-5-nonylpyrimidine,
24% of 2-p-Nonyloxyphenyl-5-nonylpyrimidine,
20% of 5-(p-Nonlphenyl)-pyrimidin-2-yl p-hexylbenzoate,
10% of 5-(p-Nonylphenyl)-pyrimidin-2yl p-heptylbenzoate,
10% of p-(5-Heptylpyrimidin-2-yl)-phenyl p-hexylbenzyl ether,
8% of p-(5-Nonylpyrimidin-2-yl)-phenyl p-heptylbenzyl ether and
10% of optically active ethyl 2-[p-nonylpyrimidin-2-yl)-phenoxy] propanoate
exhibits C −8° $S_c$* 71° Ch 88° I and a spontaneous polarization $P_s$ of 8 nC/cm² at 20°.

We claim:
1. In a ferroelectric liquid-crystalline phase comprising an achiral basic mixture and at least one optically active compound, the improvement wherein the achiral basic mixture contains at least one compound of the formula I

$$R^1—A^1—Z^1—A^2—R^2 \quad\quad I$$

wherein
$R^1$ and $R^2$ are each independently alkyl of 3 to 12 C atoms, alkyl of 3 to 12 C atoms in which one CH₂ group is replaced by —CO—, —O—CO—, O—COO—, —CO—O— or —CH=CH—, or alkyl in which one or two CH₂ groups are replaced by 0 atoms, the resulting groups having 3 to 12 C atoms,
$A^1$ is —Pyr—Phe— or —Phe—Pyr—, —Pyr—Phe— being

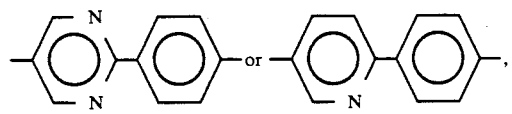

—Phe—Pyr— being

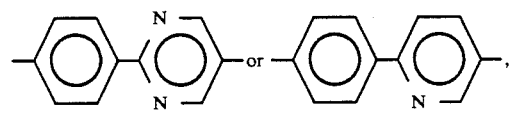

$A^2$ is trans-1,4-cyclohexylene (cy) or 1,4-phenylene (phe), and
$Z^1$ is —CH₂CH₂—, —CH₂O— or —OCH₂—, or—if $A^2$ is trans-1,4-cyclohexylene—also —O—CO—.

2. A phase of claim 1, containing at least one compound of the formulae I11, I13, or I15

| | |
|---|---|
| R—Pyr—Phe—OCH₂—Cy—R′ | I11 |
| R—Pyr—Phe—OCO—Cy—R′ | I13 |
| R—Pyr—Phe—CH₂CH₂—Cy—R′ | I15 | wherein R and R′ are straight-chain alkyl, alkoxy, alkanoyloxy or alkoxycarbonyl groups having 3 to 12 C atoms in each case.

3. A phase of claim 1, containing at least one compound of the formulae Ia or Ie

| | |
|---|---|
| R¹—Pyr—Phe—Z¹—Phe—R² | Ia |
| R¹—Phe—Pyr—Z¹—Phe—R². | Ie |

4. A phase of claim 3, containing at least one compound of the formula Iaa to Iae.

| | |
|---|---|
| R¹—Pyr—Phe—OCH₂—Phe—R² | Iaa |
| R¹—Pyr—Phe—CH₂CH₂—Phe—R² | Iab |
| R¹—Pyr—Phe—CH₂O—Phe—R². | Iac |

5. A phase of claim 3, containing at least one compound of the formulae Iea to Iec:

| | |
|---|---|
| R¹—Phe—Pyr—OCH₂—Phe—R² | Iea |
| R¹—Phe—Pyr—CH₂CH₂—Phe—R₂ | Ieb |
| R¹—Phe—Pyr—CH₂O—Phe—R². | Iec |

6. A phase of claim 1, wherein R¹ and R² are independently each alkyl, alkoxy, oxaalkyl, alkanoyloxy or alkoxycarbonyl.

7. A phase of claim 1, wherein Z¹ is —OCH₂—.

8. A phase of claim 1, wherein A² is trans,1,4-cyclohexylene.

9. A phase of claim 1 which is smectic C.

10. In a rapidly switching ferroelectric display element comprising a ferroelectric liquid crystalline phase, the improvement wherein said phase is one of claim 1.

11. A display element of claim 10, further comprising means for operation by the principle of SSFLC technology.

* * * * *

UNITED STATES PATENT AND TRADEMARK OFFICE
CERTIFICATE OF CORRECTION

PATENT NO. : 5,055,221
DATED : October 8, 1991
INVENTOR(S) : Bernhard SCHEUBLE et al.

It is certified that error appears in the above-identified patent and that said Letters Patent is hereby corrected as shown below:

Column 30, line 44 reads - - -

" of the formulae Ia or Ie "

Should read - - - -

" of the formulae Ia or Ie. "

Column 30, line 49 reads - - -

" of the formulae Iaa to Iae. "

Should read - - - -

" of the formulae Iaa to Iac. "

Signed and Sealed this

Eighth Day of June, 1993

Attest:

MICHAEL K. KIRK

*Attesting Officer*     *Acting Commissioner of Patents and Trademarks*